(12) United States Patent
Wang

(10) Patent No.: US 8,072,711 B1
(45) Date of Patent: Dec. 6, 2011

(54) SYSTEM AND METHOD FOR THE FABRICATION, CHARACTERIZATION AND USE OF MAGNETIC CORROSION AND CHEMICAL SENSORS

(76) Inventor: Jian-Qing Wang, Vestal, NY (US)

( * ) Notice: Subject to any disclaimer, the term of this patent is extended or adjusted under 35 U.S.C. 154(b) by 1272 days.

(21) Appl. No.: 11/462,034

(22) Filed: Aug. 2, 2006

(51) Int. Cl.
*G01N 27/00* (2006.01)
*G01N 25/18* (2006.01)
*G11B 5/33* (2006.01)

(52) U.S. Cl. .................. 360/324; 360/324.1; 422/82.02; 436/149

(58) Field of Classification Search ............... 422/82.02; 436/149; 360/324, 324.1
See application file for complete search history.

(56) References Cited

U.S. PATENT DOCUMENTS

| | | | | |
|---|---|---|---|---|
| 5,301,079 A | * | 4/1994 | Cain et al. ................... | 440/88 M |
| 5,583,725 A | * | 12/1996 | Coffey et al. ............ | 360/324.11 |
| 6,124,711 A | * | 9/2000 | Tanaka et al. ............... | 324/252 |
| 6,375,761 B1 | * | 4/2002 | Gambino et al. .............. | 148/301 |
| 6,462,541 B1 | | 10/2002 | Wang et al. | |
| 6,599,401 B1 | | 7/2003 | Wang et al. | |
| 6,600,637 B1 | | 7/2003 | Wang et al. | |
| 2004/0075956 A1 | * | 4/2004 | Tetsukawa et al. ........ | 360/324.1 |
| 2007/0121254 A1 | * | 5/2007 | Holman ..................... | 360/324.1 |

OTHER PUBLICATIONS

Corbett, Richard A., Laboratory Corrosion Testing of Medical Implants, Corrosion Testing Laboratories, www.corrosionlab.com/papers/medical-implant/medical-implant-testing.htm.
Davis, et al., Development of an electrochemistry-based corrosion sensor to monitor corrosion of boiler tubes, pipes, and painted structures, DACCO SCI, INC., www.daccosci.com/SPIE98.htm.
www.corrosionsource.com/technicallibrary/corrdoctors/Modules/MonitorBasics/Types.htm.
Douglas, et al., Corrosion monitoring of plutonium oxide and SNF, WM'03, Topic No. 2.4, Technical Progress . . . Long Term Storage of SNF, www.vistaengr.com/library/CorrosionMonitoringofPlutoniumOxideandSNF.pdf.
Yashiro, et al., Effect of Spatial Distribution of Electronic and Ionic Currents on the Magnetic Field Induced by Galvanic Corrosion, J. Electrochem Soc., vol. 149, Issue 3, pp. B65-B69, Mar. 2002.
Juzeliunas, et al., A SQUID Study of Magnetic Fields Resulting from In Situ Corrosion Reactions, Electrochem. Solid-State Lett., vol. 3, Issue 1, pp. 24-27 (Jan. 2000).
Weiss, Taking corrosion's magnetic pulse (research on monitoring magnetic fields associated with corrosion), Science News, Feb. 27, 1988.
www.stonerleeds.ac.uk/research/spinv.htm.
Lensveld, on the preparation and characterisation of MCM-41 supported heterogeneous nickel and molybdenum catalysts (Ph.D. Thesis, 2003) Proefschrift Universiteit Utrecht, igitur-archive.library.uu.nl/dissertations/2003-0325-143241/inhoud.htm.

* cited by examiner

*Primary Examiner* — Lore Jarrett

(57) ABSTRACT

A chemical or corrosive environment sensing system, comprising a giant magnetoresistive effect device having at least one environmentally exposed film, and a device, for sensing changes in the GMR effect device resulting from environmental exposure of the at least one environmentally exposed film. The film may be reversibly or irreversibly altered by the exposure, and is preferably nano-textured to alter a reaction rate and surface area. The sensor may be enzyme linked, that is, respond to an enzyme reaction product rather than the substrate directly. The GMR property altered and/or sensed may be, for example, a lower or upper switching field, an electrical resistance, and the GMR value. The device may be used as a sensor or as part of a control system.

21 Claims, 9 Drawing Sheets

SYSTEM AND METHOD FOR THE FABRICATION, CHARACTERIZATION AND USE OF MAGNETIC CORROSION AND CHEMICAL SENSORS

FIELD OF THE INVENTION

The present invention relates to the field of magneto-electronic based corrosion and chemical sensors.

BACKGROUND OF THE INVENTION

Corrosion causes substantial damage to devices, vehicles and infrastructure. In many cases, protective coatings are available to prevent corrosive environments from oxidizing exposed metals. However, in other cases, such coatings are unavailable or difficult to apply. This is particularly true with portable consumer electronic devices, such as cell phones, which have significant circuitry exposed to the environment, with modest voltages imposed over short distances. If the circuits in these device become immersed, especially in salt water, but even in tap water or rain, corrosion can occur which degrades performance or makes the device effectively unusable. In some cases, the faults that result are intermittent or difficult to diagnose.

Metals and alloys are commonly used as construction materials, in building, bridge, ship, oil, automotive, electric and microelectronic industries. Among others, magnetic metals, such as iron, nickel, cobalt and their alloys, are extensively used in transformers, permanent magnets and magnetic recording media. Corrosion of these media is an important problem affecting daily lives with economical consequences. There are needs for continuous improvement in the methods of corrosive detection and corrosion monitoring.

Corrosion in the atmosphere depends on air moisture and airborne impurities. To reduce the corrosion rate it is critical that corrosive species and dirt are not allowed to accumulate on the surface and thus create a wet poultice. Otherwise, this creates a situation similar to a crevice with possibility for decreased pH and high concentration of corrosive species like chlorides in a marine atmosphere, where corrosion can proceed uninterrupted. The atmosphere environment normally is classified into three categories; rural, industrial and marine. The corrosivity can vary a lot within each class depending on climate, level of pollution, distance to the sea, etc. In addition some atmospheres may be combinations of marine and industrial. In the oil and gas industry corrosion processes involve mainly water and $H_2S$. The corrosivity of fresh waters depends on the hardness and pH of the water, chloride and heavy metal concentration in addition to temperature, flow rate and $O_2$ concentration. In sea waters the main factor is the high content of chlorides. In aqueous environments microbiological organisms play an important role in corrosion. Soil corrosion, which is ascribed to low pH, stray currents, reactive chemicals, low resistivity and bacterial action, may be considered to encompass all corrosion taking place on buried structures.

Traditionally, corrosion in materials as in oil pipeline, offshore structures and vessels is monitored by various techniques such as ultrasonic thickness gauges, Eddy current imaging, X-ray tomography, and electrochemical spectroscopy techniques, designed to analyze interior microstructure and subsurface features. These techniques are less sensitive and some are quite expensive and inconvenient due to sophisticated equipment involved. There are also techniques based on in situ monitoring such as piezoelectric oscillator to measure changes in materials properties. Since the typical sensor sizes are about several micrometers, by distributing these sensors throughout a corroding surface one will be able to examine, with micrometer resolution, if the corrosion occurs locally (at micron scales) or in an uniform fashion.

Out of all the problems associated with corrosion, three aspects of corrosion detection in structures are important: (1) first, one should be able to sensitively detect the extent of corrosion taking place in a given structure at a given location and time, (2) second, one should be able to assess the total damage that has occurred and (3) third, one should assess remnant useful performance left in the structural component of the structure of interest.

The relative constancy of normal corrosion rates of different materials shows that most of the parameters for time of wetness and enhanced corrosion conditions are well defined if the composition of the corroding liquid and the involved metal is fixed. To attain more accurate data of atmospheric corrosion conditions parameters such as relativity humidity, pH and composition of condensing media and temperature need to be monitored. The development of atmospheric corrosion monitors was started a few decades ago in US and in Sweden and are usually called "time of wetness sensors" (TOWS)[1]. These designs are based on galvanic current measurement and they simply determine the periods of time during exposure of the sensors when condensation of moisture occurs on the sensors (>87% RH or relative humidity level) and leads to passage of current in a circuit, the condensate being used as a part of the circuit. In most recently manufactured corrosion sensing units, using bi-metallic thin film micro-sensors performs the monitoring of corrosion in an aggressive environment. The sensor output is essentially a polarized corrosion current of the active component in the couple (working electrode) and does only a qualitative measurement. Now such type of sensors is being employed as atmospheric corrosion sensors (ACS). It is also possible to do quantitative potentiometric measurement and corrosion rate determination by electrochemical linear polarization technique as a function of time and environmental conditions. Generally one potential close to the corrosion potential of the metal is chosen by the others and from the current passing through at this offset potential the corrosion current is determined by employing the Stern-Geary equation[1]. However, in all these methods no consideration was given to the corrosion product buildup and the corrosion potential variation as a function of time and the corrosion process itself. As a result the inferences obtained and the data generated could not be construed as very accurate.

ASTM G 31 7 is an immersion test procedure that typically requires extended exposure periods, up to years, to evaluate the resistance of materials, which are employed in the implant device industry, to corrosion. As such, accelerating the testing by inducing changes on the material and monitoring the results has been an industry-accepted method. The development of accelerated electrochemical tests to study corrosion began in earnest during the late 1960's and into the 1980's in the CPI. The original test standard, ASTM G 5, 8 was expanded from a stepped potentiostatic test to a potentiodynamic test as electronics developed, and subsequently to a cyclic experiment to examine susceptibility to localized pitting and crevice corrosion [ASTM G 61 9]. Galvanic studies between mixed metals in contact with each other were evaluated using the established ASTM G 71 10. See, Richard A. Corbett, "Laboratory Corrosion Testing of Medical Implants", Corrosion Testing Laboratories, www.corrosionlab.com/papers/medical-implant/medical-implant-testing-.htm.

Corrosion sensors are typically electrochemical, and rely on changes in conductivity, resistivity, or redox potential to determine or predict corrosion. See, G. D. Davis, C. M. Dacres, and M. B. Shook, "Development of an electrochemistry-based corrosion sensor to monitor corrosion of boiler tubes, pipes, and painted structures", DACCO SCI, INC. (www.daccosci.com/SPIE98.htm), expressly incorporated herein by reference.

Corrosion monitoring is the practice of measuring the corrosivity of process stream conditions by the use of "probes" which are inserted into the process stream or environment to be measured and which are continuously exposed to the conditions. Corrosion monitoring "probes" can be mechanical, electrical, or electrochemical devices. These "probes" serve as a proxy for other elements of the system which are presumed to corrode in a corresponding manner to the probes. In some cases, the probe may be an actual element of interest, and indeed, all potentially corroding elements may be sensors. See, www.corrosionsource.com/technicallibrary/condoctors/Modules/MonitorBasics/Types.htm. The nature of the sensors depends on the various individual techniques used for monitoring but often a corrosion sensor can be viewed as an instrumented coupon. In older systems, electronic sensor leads were usually employed for these purposes and to relay the sensor signals to a signal-processing unit. Advances in microelectronics are facilitating sensor signal conditioning and processing by microchips, which can essentially be considered to be integral to the sensor units. Some corrosion measurement techniques can be used on-line, constantly exposed to the process stream, while others provide off-line measurement, such as that determined in a laboratory analysis. Some techniques give a direct measure of metal loss or corrosion rate, while others are used to infer that a corrosive environment may exist. Real-time corrosion measurements refer to highly sensitive measurements, with a signal response taking place essentially instantaneously as the corrosion occurs. Numerous real-time corrosion monitoring programs in diverse branches of industry have revealed that the severity of corrosion damage is rarely uniform with time. Complementary data from other relevant sources, such as process parameter logging and inspection reports can be acquired together with the data from corrosion sensors, for use as input to the management information system.

Known techniques include:

A. Direct techniques

1) Corrosion Coupons (intrusive) (samples are monitored for weight loss due to corrosive loss of material).

2) Electrical Resistance (ER) (intrusive) (measures the change in electrical resistance of a metallic element immersed in a product media relative to a reference element sealed within the probe body).

3) Inductive Resistance Probes (intrusive) (Mass changes in a sensor element are detected by measuring changes in the inductive resistance of a coil, located inside the element).

4) Linear Polarization Resistance (LPR) (intrusive) (a small voltage, or polarization potential, is applied to an electrode in solution and the current needed to maintain a specific voltage shift (typically 10 mV) is directly related to the corrosion on the surface of the electrode in the solution. By measuring the current, a corrosion rate can be derived.)

5) Zero Resistance Asymmetry (ZRA) (intrusive) (In ZRA, also known as galvanic monitoring, two electrodes of dissimilar metals are exposed to the process fluid. When immersed in solution, a natural voltage (potential) difference exits between the electrodes. The current generated due to this potential difference relates to the rate of corrosion which is occurring on the more active of the electrode couple.)

6) Electrochemical Impedance Spectroscopy (EIS) (intrusive) (an alternating potential perturbation is applied to one sensor element in a three-element probe, with a resultant current response, to measure the impedance.)

7) Harmonic Analysis (intrusive) (Higher order harmonic analysis of EIS method)

8) Electrochemical Noise (EN) (intrusive) (EN corrosion monitoring tracks extremely small current and voltage fluctuations among three electrodes, made of material as similar as possible to the waste tank material, placed in the waste solution. Current is measured between two electrically coupled electrodes (a working electrode and a counter electrode), while the third electrode is connected between the working electrode and a pseudo-reference electrode to measure the voltage. The magnitude and polarity of the signals, as well as the relationship of the timed signal traces to each other, provide indicators of type and significance of the corrosion processes occurring in the tank. Particular types of corrosion have unique and potential "signatures" that indicate when pitting or stress corrosion cracking is occurring.)

9) Potentiodynamic Polarization (intrusive) (measurement of current through a sample with a change in applied voltage potential. An initial static potential is measured, and a scan made from an initial potential of 100 mV below the one-hour potential, in the positive (active to noble) direction at a rate of e.g., 0.16 mV per second, and then reversed when the current has reached two decades greater than that of the breakdown potential [$V_b$] (defined as a rapid increase of current per increment of applied potential). The reverse scan is stopped when the current becomes less than the current in the forward scan (defined as the protection potential, Vp) or the potential reaches the initial potential. The data is plotted on an x-y semi logarithmic diagram with the current density on the x-axis [logarithmic] in $mA/cm^2$ and the potential versus a SCE on the linear y-axis. Appropriate references in their final form and finish are used as controls.)

10) Thin Layer Activation (TLA) and Gamma Radiography (intrusive or non-intrusive) (In this technique developed from the field of nuclear science, a small section of material is exposed to a high energy beam of charged particles, to produce a radioactive surface layer. For example, a proton beam may be used to produce the radioactive isotope Co-56 within a steel surface. This isotope decays to Fe-56, with the emission of gamma radiation. The concentration of radioactive species is sufficiently low, that metallurgical properties of the monitored component are essentially unchanged. The radioactive effects utilized are at very low levels and should not be compared to those of conventional radiography. The change in gamma radiation emitted from the surface layer is measured with a separate detector to study the rate of material removed from the surface. The radioactive surfaces can be produced directly on components (non-intrusive) or on separate sensors).

11) Electrical Field Signature Method (EFSM) (non-intrusive) (The technique measures corrosion damage over several meters of an actual structure, clearly distinguishing it from other smaller sensor systems. An induced current is fed into the monitored section of interest and the resulting voltage distribution is measured to detect corrosion damage. An array of pins is attached strategically over the structure for measuring purposes. Increased pin spacing implies lower resolution for localized corrosion. Typical applications involve pin attachment to the external surface of a pipeline, to monitor corrosion damage to the inside of the pipe walls.)

12) Acoustic Emission (AE) (non-intrusive) (measurement of acoustic sound waves emitted during the growth of microscopic defects, such as stress corrosion cracks. The sensors act as microphones, positioned on structures, which detect sound waves generated from mechanical stresses generated during pressure or temperature changes.)

B. Indirect techniques

1) Corrosion Potential (non-intrusive) (The corrosion potential of the element to be monitored is measured relative to a reference electrode, which is characterized by a stable half-cell potential.)

2) Hydrogen Monitoring (non-intrusive) (The generation of atomic hydrogen, as part of the cathodic half-cell reaction in acidic environments. Hydrogen monitoring probes are based on either of the following three principles: pressure increase, electrochemical current resulting from the oxidation of hydrogen under an applied potential, and current flow in an external circuit, based on a fuel cell principle.)

3) Chemical Analyses (e.g., pH, conductivity, dissolved oxygen, metallic and other ion concentrations, water alkalinity, concentration of suspended solids, inhibitor concentrations and scaling indices)

4) Corrosion sensors are typically electrochemical, and rely on changes in conductivity, resistivity, or redox potential to determine or predict corrosion. See, G. D. Davis, C. M. Dacres, and M. B. Shook, "Development of an electrochemistry-based corrosion sensor to monitor corrosion of boiler tubes, pipes, and painted structures", DACCO SCI, INC. (www.daccosci.com/SPIE98.htm), expressly incorporated herein by reference.

5) Certain "magnetic" corrosion sensors are known, for example a mechanical breakage sensor whose output is magnetically coupled through a vessel wall. See, Dennis G. Douglas, Christopher M. Smith, Phillip C. Ohl, Carey M. Haas (Vista Engineering Technologies, LLC), "CORROSION MONITORING OF PLUTONIUM OXIDE AND SNF", WM'03—Topic No. 2.4, Technical Progress . . . Long Term Storage of SNF, www.vistaengr.com/library/CorrosionMonitoringofPlutoniumOxideandSNF.pdf.

6) In addition, a number of sensors detect a current or magnetic field induced by a current with a superconducting quantum interference device (SQUID). See, e.g., Hitoshi Yashiro, Masahito Yoshizawa, Naoaki Kumagai, and Johann H. Hinken, "Effect of Spatial Distribution of Electronic and Ionic Currents on the Magnetic Field Induced by Galvanic Corrosion", J. Electrochem. Soc., Volume 149, Issue 3, pp. B65-B69 (March 2002); Eimutis Juzeliunas, Meilute Samuleviciene, Aloyzas Sudavicius, and Johann H. Hinken, "A SQUID Study of Magnetic Fields Resulting from In Situ Corrosion Reactions", Electrochem. Solid-State Lett., Volume 3, Issue 1, pp. 24-27 (January 2000); Weiss, Rick, "Taking corrosion's magnetic pulse. (research on monitoring magnetic fields associated with corrosion)", Science News; Feb. 27, 1988.

Recent progresses in magnetic field sensing, and magnetic materials research lend new technologies in monitoring corrosion. One idea consists of detecting changes in magnetic properties due to corrosion of specially designed magnetic materials. Because the corrosion products of magnetic materials are generally nonmagnetic or with distinctly different measuring the changes in these properties by corrosion can be a sensitive tool.

The Giant Magneto Resistance (GMR) effect was discovered in 1988 and it is the phenomenon where the resistance of certain materials drops dramatically as a magnetic field is applied. It is described as Giant since the effect is much larger than in regular metals. It has generated strong interests in research community, as there are perspectives both in exploring new physics and technological applications as in magnetic recording and sensors. The effect is seen in spin-valve structures, where two magnetic layers are closely separated by a thin non-magnetic spacer of a few nanometer thickness. It is analogous to a light polarization experiment, where aligned polarizers allow light to pass through, but crossed polarizers do not. A magnetic layer allows electrons in only one spin state to pass through easily. If the second magnetic layer is aligned then that spin channel can easily pass through the structure, and the resistance is low. If the second magnetic layer is misaligned then neither spin channel can get through the structure easily and the electrical resistance is high. The GMR effect effectively measures the difference in the angle between the two magnetic orientations in the magnetic layers, with small angles (parallel) giving low resistance, and large angles (antiparallel) giving higher resistance. This angle depends on the applied magnetic field, and thus the change in the magnetoresistance can be used to measure magnetic fields. In GMR spin-valve materials $\Delta R/R$ values of more than 65% at the ambient temperature have been reported. Since the sensitivity of a sensor is proportional to $\Delta R/R$, the advantages of these GMR materials for field sensing is obvious.

U.S. Pat. No. 6,599,401, Wang, et al. (having a common inventor with the present application), expressly incorporated herein by reference, provides an in-plane anisotropic tri-layered magnetic sandwich structure which demonstrates a large magnetoresistance effect. Fe/Co/Cu/Co magnetoresistive structures deposited on Si (100) substrates were found to demonstrate uniaxial magnetic anisotropy. Samples magnetized along an easy anisotropy axis showed extremely sharp magnetization, and corresponding magnetoresistance, switching at low fields and maximum giant magnetoresistance of 9.5% at 5K (5.5% at room temperature) for the samples with 5 nm of Fe, 5 nm of Co, 2.5 nm of Cu and 2 nm of Co.

A GMR effect sensor is proposed in Wang et al., U.S. Pat. No. 6,462,541, expressly incorporated herein by reference. Wang et al., suggest a uniform sense condition magnetic field sensor using differential magnetoresistance. A ferromagnetic thin-film based sensing arrangement having a plurality of magnetic field sensors on a substrate, each having an intermediate layer of a nonmagnetic material with two major surfaces on opposite sides thereof, with one of a pair of permeable films each formed of a magnetoresistive, anisotropic ferromagnetic material correspondingly positioned thereon, with first and second oriented sensors therein respectively having a selected and a reversing magnetization orientation structure provided with one of the pair of permeable films thereof, for orienting its magnetization in a selected direction absent an externally applied magnetic field in at least partly opposing directions. The magnetizations of those films rotates over a smaller angle in a selected externally applied magnetic field present thereat than does the magnetization orientation of the other permeable film in the pair. The first and second oriented sensors are electrically connected between a pair of terminating regions suited for electrical connection across a source of electrical energization. Alternatively, these magnetizations of the films can be oriented in the same direction but with the other film member of the pair provided adjacent a coupling layer that antiferromagnetically couples thereto a further ferromagnetic layer on an opposite side thereof of a lesser thickness for one sensor, and a greater thickness for the other. The intermediate layer material can be either a conductive material or a dielectric material. Such a sensing arrangement can be formed by providing a succession of material layers on a substrate having therein the intermediate layer and the pair of permeable films, with the one of the pair of permeable films being adjacent a succession of magnetization orientation layers having at least one coupling layer for antiferromagnetically coupling ferromagnetic layers on opposite sides thereof. Removal of some of the succession to provide an unequal number of coupling layers between locations for the two kinds of sensors, or unequal thicknesses of corresponding ferromagnetic layers corresponding to the coupling layer, is followed by providing a pinning layer at both kinds of locations. Removal of the succession at other locations results in providing the two kinds of sensors.

U.S. Pat. No. 6,600,637 (Wang et al.), expressly incorporated herein by reference, relates to a magnetoresistive sensor for a magnetic storage system having an edge barrier to prevent spin valve corrosion. During fabrication of a transducing head, Wang et al. report that the MR sensor is subjected to many processing steps. Current contacts and biasing layers are commonly deposited adjacent to the MR sensor after the MR sensor is shaped, but before the second half gap is deposited. The formation of the contacts and biasing layers, as well as the patterning of the MR sensor itself, subjects the MR sensor to a harsh environment that may result in corrosion of the MR sensor. This is particularly true of a multi-layered sensor such as a spin valve sensor.

Multi-layered sensors generally are formed of multiple materials, several of which very easily corrode. Since an MR sensor relies on the existence of each of its layers to operate properly, corrosion of any of its layers will result in the sensor having a reduced amplitude, a distorted signal output, decreased stability, and/or increased noise. They do not suggest that this corrosion may be intentionally exploited, nor that conditions other than those of manufacture may have an effect on the sensor.

Spin valves are a type of solid state magnetic field sensors. See, www.stoner.leeds.ac.uk/research/spinv.htm. A spin valve is, in general, a sample consisting essentially of a GMR trilayer. One layer is magnetically soft—meaning its magnetization is very sensitive to small fields. The other is made magnetically 'hard' by various schemes—meaning it is insensitive to fields of moderate strength. As the soft 'free' layer changes its magnetic state, due to applied fields, the resistance of the whole structure will vary. The central part of the sample consists of two magnetic layers (e.g., permalloy with a thin covering of Co), separated by a Cu spacer layer. One magnetic layer is pinned or exchange biased by an antiferromagnetic material, e.g., FeMn and IrMn.

Spin valves are dedicated GMR systems, in which the electrical resistance is high or low, depending on the direction rather than the strength of the magnetic field. Contrary to water valves they are not fully open or closed, the change in resistance is typical in the range of 5% to 10%. A spin valve is typically made of only two ferromagnetic layers spaced by a layer of nonmagnetic metal. Contrary to a GMR multilayer, the two ferromagnetic layers are magnetically coupled. As a further difference the magnetization of one of the ferromagnetic layers is spatially fixed ("pinned") by an antiferromagnetic bottom layer. Thus it is called the "pinned layer", the other is called the "free layer", because it should easily follow the external magnetic field.

The resistance in the plane of a ferromagnetic thin-film is isotropic with respect to the GMR effect rather than depending on the direction of a sensing current therethrough as for the anisotropic magnetoresistive effect. The GMR effect has a magnetization dependent component of resistance that varies as the cosine of the angle between magnetizations in the two ferromagnetic thin-films on either side of an intermediate layer. In the GMR effect, the electrical resistance through the "sandwich" or superlattice is lower if the magnetizations in the two separated ferromagnetic thin-films are parallel than it is if these magnetizations are antiparallel, i.e. directed in opposing directions. Further, the anisotropic magnetoresistive effect, also present in GMR structures in very thin-films, is considerably reduced from the bulk values therefor in thicker films due to surface scattering, whereas very thin-films are a fundamental requirement to obtain a significant GMR effect. The GMR effect can be increased by adding further alternate intermediate and ferromagnetic thin-film layers to extend the "sandwich" or superlattice structure. The GMR effect is sometimes called the "spin valve effect" in view of the explanation that a larger fraction of conduction electrons are allowed to move more freely from one ferromagnetic thin-film layer to another if the magnetizations in these layers are parallel than if they are antiparallel with the result that the magnetization states of the layers act as sort of a valve.

In magnetic multilayers, these magnetization configurations often come about because of magnetic exchange coupling between the ferromagnetic thin-films separated by the intermediate layers, these intermediate layers typically formed from a nonferromagnetic transition metal. The effect of the exchange coupling between the ferromagnetic thin-film layers is determined to a substantial degree by a function of the thickness of the intermediate layer, which oscillates as a function of the separation thickness between ferromagnetic coupling and antiferromagnetic coupling. In spin valves, such exchange coupling is not as obvious, although Wang reported exchange coupling does affect the soft magnetic layer switching with applied magnetic field in pseudo spin valves.

The ferromagnetic thin-film layers may be formed with alternating high and low coercivity materials so that the magnetization of the low coercivity material layers can be reversed without reversing the magnetizations of the others. An alternative arrangement is to provide "soft" ferromagnetic thin-films and couple antiferromagnetically every other one of them with an adjacent magnetically hard layer (forming a anti-ferromagnetic thin-film double layer) so that the anti-ferromagnetic double layer will be relatively unaffected by externally applied magnetic fields even though the magnetizations of the other ferromagnetic thin-film layers will be subject to being controlled by such an external field. A multilayer structure may be provided that is etched into strips such that demagnetizing effects and currents can be used to orient the magnetizations antiparallel, and so that externally applied magnetic fields can orient the magnetizations parallel. Thus, parallel and antiparallel magnetizations can be established in the ferromagnetic thin-films of the structure as desired in a particular use. Such a structure must be fabricated so that any ferromagnetic or antiferromagnetic coupling between separated ferromagnetic films is not too strong so as to prevent such establishments of film magnetizations using practical interconnection arrangements.

A magnetic field sensor suited for fabrication with dimensions of a few microns or less can be fabricated that provides a suitable response to the presence of very small external magnetic fields and low power dissipation by substituting an electrical insulator for a conductor in the nonmagnetic layer. This sensor can be fabricated using ferromagnetic thin-film materials of similar or different kinds in each of the outer magnetic films provided in a "sandwich" structure on either side of an intermediate nonmagnetic layer which ferromagnetic films may be composite films, but this insulating intermediate nonmagnetic layer permits electrical current to effectively pass therethrough based primarily on a quantum electrodynamic effect "tunneling" current.

This "tunneling" current has a magnitude dependence on the angle between the magnetization vectors in each of the ferromagnetic layers on either side of the intermediate layer due to the transmission barrier provided by this intermediate layer depending on the degree of matching of the spin polarizations of the electrons tunneling therethrough with the spin polarizations of the conduction electrons in the ferromagnetic layers, the latter being set by the layer magnetization directions to provide a "magnetic valve effect". Such an effect results in an effective resistance, or conductance, characterizing this intermediate layer with respect to the "tunneling" current therethrough. The maximum fractional change in effective resistance is a function of the magnetic polarization of the conduction electrons given by $(\Delta R/R)=2P_1 P_2/(1+P_1 P_2)$, where $P_1$ and $P_2$ are the conduction electron spin polarizations of the two ferromagnetic layers. These polarizations appear dependent on the ratio of spin up to spin down electrons in the 3D shell of the transition elements used in the ferromagnetic thin-films, i.e. the spin polarization P of the conduction electrons. The fraction f of 3D electrons which are spin up have typical values of 0.75 for iron, 0.64 for cobalt and 0.56 for nickel. Conduction electrons in metals are normally S shell electrons which theoretically would be equally divided between spin up and spin down electrons. However, because of band splitting the conduction electrons in the magnetic layers are assumed to have a fraction of spin up electrons like that of the electrons in the 3D shell. The spin polarization is then determined from $P=2f-1$.

In addition, shape anisotropy is often used in such a sensor to provide different coercivities in the two ferromagnetic layers, and by forming one of the ferromagnetic layers to be thicker than the other. Such devices may be provided on a surface of a monolithic integrated circuit to thereby allow providing convenient electrical connections between each such sensor device and the operating circuitry therefor.

A "sandwich" structure for such a sensor, based on having an intermediate thin layer of a nonmagnetic, dielectric or otherwise, separating material with two major surfaces on each of which a anisotropic ferromagnetic thin-film is positioned, exhibits the "magnetic valve effect" if the materials for the ferromagnetic thin-films and the intermediate layers are properly selected and have sufficiently small thicknesses. The resulting "magnetic valve effect" can yield a response which can be several times in magnitude greater than that due to the "giant magnetoresistive effect" in a similar sized sensor structure.

The current-voltage characteristics of such "sandwich" structure sensors will exhibit a relatively linear change in the quantum electrodynamic effect "tunneling" current therethrough from one ferromagnetic layer through the barrier to the other with respect to the voltage provided across the sensor, i.e. across the barrier layer between these ferromagnetic layers, for relatively lower value voltages, but the current magnitude increases more than linearly for higher values of voltage across the sensor. As the voltage across the sensor increases, the fractional change in the "tunneling" current through the sensor, for the ferromagnetic layers having magnetizations changing from parallel to one another to antiparallel, decreases to being only half as great with several hundred millivolts across the sensor as occurs in the situation with a hundred or less millivolts across the sensor so that this fractional change with sensor voltage will range from a few percent to 20% or more. The fractional change in the resistance of the sensor for the ferromagnetic layers having magnetizations changing from parallel to one another to antiparallel increases to about one and one-half the room temperature values when the sensor is cooled to 77° K, but the "tunneling" current through the sensor increases by only about 10% to 20% indicating that the effective resistivity of the sensor is relatively insensitive to temperature (around 500 to 1000 ppm/° C.).

The effective resistivity of such a sensor is set by the amount of "tunneling" current through the cell permitted by barrier layer for the voltage across the sensor. The high sensitivity of the "tunneling" current to the thickness of the barrier layer leads to a wide range of sensor resistivities which have been observed to be from $60.0\Omega\text{-}\mu m^2$ to $10,000\ M\Omega\text{-}\mu m^2$. On the other hand, the barrier layer appears to permit relatively weak magnetic coupling between the ferromagnetic layers thereacross with the coupling fields typically being only a few Oe.

The barrier material for such sensing devices has typically been aluminum oxide, $Al_2O_3$ and other such oxides, but other dielectric materials have been used. A typical construction therefore has had two long rectangular ferromagnetic thin-film strips with the barrier layer therebetween such that the long axis of the bottom strip, supported directly on an electrically insulating substrate, at some angle with respect to that of the upper strip supported thereon through the barrier layer. This arrangement leaves the crossover area where these ferromagnetic strips overlap having the shape of a parallelogram defining the portion of the barrier layer through which there is effective current tunneling between the strips.

These devices are fabricated by depositing upon the insulating substrate a narrow stripe of the bottom ferromagnetic film typically using a separate, removable mask. A layer of dielectric material is then formed over this bottom film, and then a second narrow stripe ferromagnetic film is deposited through a mask such that the long direction axis of the second stripe is, typically, perpendicular to that of the first. The region of tunneling between the two stripes is then typically shaped as square or rectangle where the two stripes overlap. The shape of the interposed dielectric barrier is inconsequential so long as it is sufficiently large to completely separate the two ferromagnetic thin-film metal stripes. The ferromagnetic layers in these structures are typically simple single films of Fe, Co, NiFe or other common ferromagnetic alloys.

Generally, fabricating a very small overlap area in such sensors using masking techniques is difficult to accomplish because of deposition material spatial distribution variances which can lead to electrical short circuits between the strips. As a result, overlap area, or tunnel junction, dimensions are often of many millimeters in length and relatively thick barrier layers are needed.

The operating current for such sensors is typically supplied through a pair of current leads with one such lead connected to an end of the upper strip and the other lead connected to an end of the lower strip. The effective electrical resistance of the sensor is determined from measuring the voltage across the tunnel junction at two voltage leads each connected to one of the remaining two ends of these strips. Then, by providing a current of a known fixed value through the current leads and measuring the corresponding tunnel junction voltage on the voltage leads, the effective resistance can be simply calculated by dividing the measured voltage value by the chosen fixed current value.

Because, as indicated above, the conduction of current across the barrier of such a sensor is due to a quantum electrodynamic tunneling effect, the conduction turns out to be highly dependent on the thickness of the barrier. An increase of 2 Å in the barrier thickness can lead to an increase the junction resistance by a factor of 10. The measured resistances of tunnel junctions fabricated from the same starting material are inversely proportional to the areas of those junctions. Typical tunneling resistivities ($\rho_T$, calculated by multiplying the resistance by the tunnel junction area) range from $10^{-2}$ to $10^{-3}$ M$\Omega$-$\mu m^2$. These resistivities correspond to $Al_2O_3$ thickness of about 12 to 30 Å, respectively. Due to the sharp dependence of tunnel resistivity on the barrier thickness, $\rho_T$ can easily vary across a single wafer by a factor of two.

As indicated above, the measured resistance of the tunnel junction in such a sensor is a function of the relative orientation of the magnetizations of the two ferromagnetic thin-film metal strips. The portion of the tunnel junction resistance that is subject to change as a result of that junction experiencing changes in external magnetic fields to which it is exposed is termed junction magnetoresistance (often written JMR, and defined as $\Delta R/R_{min}$ but is equivalently $\Delta R/R_{min}$ for voltage measurements with a fixed current with either being expressed as a percentage). The sensors described above demonstrated that the JMR therefore can be quite large at room temperature (>25%).

However, such sensors cannot be conveniently incorporated into integrated circuits because the sputter-mask mode of fabrication is not compatible with modern semiconductor fabrication. In addition, the magnetic response of these sensors is not optimized for applications. In particular, they exhibit considerable hysteresis, nonlinearity and other non-ideal aspects in their JMR response, including small signal output and low areal density, as have the tunnel junction field sensor structures of subsequent designs.

A better magnetic field sensor can be made using modern semiconductor fabrication techniques having a junction structure in a sensor cell based on a nonmagnetic intermediate separating material with two major surfaces on one of which is a base anisotropic ferromagnetic thin-film which is also on a base electrode, and on the other of which there is at least one of a plurality of separate anisotropic ferromagnetic thin-films but of differing effective coercivities. The nonmagnetic intermediate separating material can be either a conductive material leading to a GMR device or an insulator leading to a spin dependent tunneling device. Similar structures have a separate film in each that can be interconnected to one another with the interconnections extending at least in part substantially parallel to the widths of the separated films. The base electrode and the separated films can have lengths with gradually narrowing widths toward each end which narrow to zero at the ends. The intermediate material supported on a base electrode can be common to all the separated films thereon.

Often more than one such magnetic field sensor is used in a sensing configuration to provide a larger output signal and, in many instances, to provide some sensor noise cancellation. These goals are many times pursued through use of a bridge circuit in which such GMR effect structures or spin dependent tunneling structures are provided as circuit resistors connected in two parallel branches between two power supply nodes with each such branch having two such resistors in series with one another. A single polarity voltage source is typically connected between the two power supply nodes with in many instances the negative side of the source being grounded. A signal sensing differential amplifier with a pair of inputs is typically electrically connected between the two bridge circuit output nodes, i.e. the internal nodes of each of the two branches which for each is the node between the two resistors connected in series therein.

To have such a bridge circuit operate properly, adjacent ones of the magnetoresistors in the circuit must vary in resistance differently under an applied magnetic field if a signal output is to result. If they each have the same resistance variation, there will be a zero value signal developed between the bridge circuit output nodes, i.e. between the sensing amplifier inputs. Since an externally applied magnetic field to be sensed will be approximately the same for each of the closely spaced resistors in the bridge circuit, design measures are necessary to assure the needed resistive differences nevertheless occur between the adjacent circuit structures or resistors. One such measure previously used has been to place two of these magnetoresistors on opposite sides of the bridge circuit each connected to different power supply terminals under a magnetic shield leaving only the other two such resistors exposed to the effects of externally applied magnetic fields. Such an arrangement, however, results in a smaller output signal for an applied eternal field than would otherwise be possibly available since two resistors are not being used to sense that field. Furthermore, provision of such shields adds risk to the fabrication process since they must be relatively large structures formed after most other steps are completed. Thus, there is a desire to obtain the needed resistive differences between the adjacent circuit structures or magnetoresistors while obtaining the full possible output signal without having to fabricate shielding structures.

SUMMARY OF THE INVENTION

The present invention permits a versatile, miniature, and easily-interfaced device to sense corrosive conditions, and thus permit a self-diagnostic for corrosion in a variety of devices, such as cell phones, laptop computers, personal computers, servers, automobiles and vetronics, telephone equipment, and other equipment subject to corrosive environments.

The sensing system and method according to the present invention may also be used to detect chemical species, for example in biomedical, chemical, and other industrial environments, to measure chemical emissions and presence of hazardous chemicals, for use in internal combustion engines, fuel cells, and systems incorporating such subsystems. Likewise, the sensing function may be used to detect chemical breakdown of fluids, such as refrigerants and lubricants, especially where the breakdown results in production of corrosive species.

According to a preferred embodiment of the invention, the sensor acts as a variable resistor, and thus is readily interfaced with various sensing systems. While the sensor is sensitive to magnetic fields, typically these can be shielded using a high magnetic permeability allow casing. However, in some cases, the magnetic sensing properties may be advantageously employed, for example to modulate the output signal, provide a means for calibration, provide a gradient of sensing conditions, or the like.

The present invention provides a magneto-electronic sensor comprising a spin valve comprising a giant magnetoresistive effect structure having a first magnetic layer and a second magnetic layer, the first and second magnetic layers being separated by a thin non-magnetic layer, and an electrical sensor for sensing a resistance of the spin valve structure, wherein one magnetic layers is chemically exposed to an environment, and the resistance and its field response of the spin valve being are dependent on the chemical properties of the environment. For example, the spin valve may be used to sense corrosion, e.g., a chemical tendency to oxidize or reduce metals, analytes, enzyme or microbial products, etc. The sensor may respond in real time to environmental conditions, or the output may represent a time-weighted exposure. Processing of the output may also permit measurement of both, as well as calibration and standardization. The sensor may respond reversibly or irreversibly to the environmental conditions.

The idea of a magnetic sensor for corrosion testing consists of the utilization of changes in magnetic properties due to corrosion of specially designed magnetic materials to monitor their corrosion rates. Because most of the corrosion products of magnetic materials are non-magnetic or they have distinctly different magnetic properties, the change of their saturation magnetization, initial permeability or coercive field caused by corrosion can be a sensitive tool for corrosion detection. One important advantage is that the magnetic sensor can monitor the corrosion of both conducting and non-conducting materials. Though the corrosion sensor embodiment of the invention is typically designed for the atmospheric corrosion testing, similar devices can also be used to monitor different kinds of corrosion environments, e.g., in toxic gaseous and aqueous environments, or microbially influenced corrosion.

The present invention provides techniques for corrosion detection by monitoring the changes in the magnetic properties in nano-structured magnetic corrosion media. The preferred technique for monitoring employs GMR sensors to measure the magnetization. The applications for the present invention include environment watch, toxic waste cleaning, pollution control, and those for military uses as in naval warfare, corrosion monitoring/protection of battleship and aircraft, submarine tracing, and chemical warfare protection, as well as many other commercial applications.

To fulfill the needs for sensitive monitoring of corrosive environments and quantitative detection of slight corrosion occurring in materials, new classes of corrosion sensors based on detecting changes in magnetic properties using ultra-sensitive magnetic field sensors are provided. The proposed corrosion sensors are based on the fact that magnetic materials are highly reactive with chemical environments and the corrosion products usually have drastically different properties. Structuring materials into submicrometer or nanometer sized arrays will generate specific measurable magnetic properties which are strongly dependent on the geometry, dimensions, and length scales. The miniaturized structures also have enhanced surface area and sensitivity to corrosions at atomic scale The present invention provides a spin valve corrosion sensor comprising a three layer GMR structure, at least one of the layers being exposed to a potentially corrosive environment, wherein the GMR response of the device varies in accordance with an extent of corrosion. In this case, corrosion is used to mean a chemical change in the thin film layer which leads to a change in magnetic properties. The sensing film may be provided with an access structure for coupling the film to the potentially corrosive environment. The sensor may also serve as a chemical sensor, for example sensing a level or cumulative exposure to a corrosive ion, or as coupled to a selective chemical reaction which generates a corrosive effect. Thus, for example, an immobilized enzyme may be provided adjacent to the sensing film, which produces, for example, hydrogen peroxide or a free radical product upon response to a substrate. The hydrogen peroxide or free radical reacts with the film to alter its magnetic properties. In some instances, the "corrosive" effect can be reversible, and thus the sensor respond to exposure rather than cumulative exposure. Of course, by differentiating the output of the sensor, the cumulative response may be converted into a current response.

The preferred sensors are based on nano-structured magnetic materials, such as patterned arrays or magnetic ion loaded meso-porous media. These materials are chosen for corrosion testing for four important reasons: (1) Magnetic grains with dimensions below 150 nm can be single domains, simplifying the interpretation of the magnetic behavior; (2) With well defined microstructure they provide highly repeatable results for a very corrosive environment by avoiding stress-corrosion and pitting corrosion mechanisms; (3) Due to very small corroding feature sizes the sensitivity will be enhanced, since the nanometer thick oxidation layers formed on magnetic metals is comparable to the characteristic sizes of the materials; and (4) The nano-sized and meso-porous materials have larger surface area, which can be orders of magnitude larger than poly-crystalline alloys. The corrosion rate can be varied with the feature size of the corroding materials, tailored to have suitable response for different materials. The materials for corrosion testing will be produced in magnetic thin film forms with submicrometer thickness.

The thin films may be made using the magnetron sputtering deposition system. This technique allows production of a large variety of thin films with repeatable microstructures (epitaxial or polycrystalline) and compositions. Sub-micron arrays and micronsized device structures will be patterned using the X-ray lithography and ion milling. The mesoporous media named MCM-41 can be made by chemical methods. They are received from hexagonal arrays of micellar rods, which are used as templates for silicon oxide growth and after removing the organic medium by calcination they form an array of tubes with diameters of 2 to 10 nm. These tubes can be loaded by ferromagnetic materials as corrosion media. See, Dennis Lensveld, "On the preparation and characterisation of MCM-41 supported heterogeneous nickel and molybdenum catalysts (Ph.D. Thesis, 2003) Proefschrift Universiteit Utrecht. igitur-archive.library.uu.nl/dissertations/2003-0325-143241/inhoud.htm.

An important consideration is the sensitivity of the sensors to detect changes in the magnetic corrosion media in corrosion. If we assume that magnetic particles fill a porous medium or a patterned magnetic array structure with 50% magnetic volume, the estimated induced magnetic field for an out-of-plane polarized medium can be as high as 700 Gauss. This value is two orders of magnitude higher than the earth magnetic field. In this estimate, the effects of decreases in Curie temperature and spontaneous magnetization due to small particle sizes, of aspect ratio of the film thickness and lateral dimensions, and typical distance between the field sensor and corrosion layer are considered. This field is strong enough to be easily detected by GMR sensors. When one atomic layer on the magnetic particle surfaces are fully corroded the change in the overall magnetization can be as large as 30% due to a large surface area. This corresponds to a field variation of 210 Gauss. For the case of an in-plane magnetized medium, the induced magnetic field is reduced further by about 0.2 for an aspect ratio of 10 (one-micron thick corrosion film with a ten-micron width). The total induced field and its variation for one atomic layer corrosion correspond to, respectively, 140 and 40 Gauss. These values can be further enhanced by decreasing the lateral dimensions of the magnetic corrosion media and by positioning the field sensors closer to the corrosion media. Thus, according to the present invention, the effect of corrosion may be enhanced over a simple planar film. It is further noted that the sensor may support creation of microenvironments, and indeed a composite sensor having various sensing elements, which, e.g., may vary incrementally in properties, may be supported. For example, an array of sensing elements may be provided, each being subjected to an incrementally varying electrochemical potential. Thus, techniques drawn from traditional corrosion sensing technologies, e.g., detailed hereinabove, may also be applied in conjunction with the thin film magnetic sensor according to the present invention. The GMR sensor has a very high frequency response, and therefore a sensor noise analysis may be particularly useful, both to gain sensitivity and avoid baseline drift and low frequency noise, and because the corrosion process may include discrete events which give rise to temporal variations and/or a pattern. The use of a nanostructured film may also give rise to resonances and other patterns which may differ, qualitatively or quantitatively, from unstructured films, and films structured with different patterns and characteristic spacings.

The parallel magnetization configuration is required for spin-valve and spin-tunneling sensors. These structures are the most sensitive field sensing devices known to date, ideally suited for the parallel magnetization configuration. To achieve such sensitivity, the patterning mini-structures with micrometer sizes are useful. The common technique of photolithography has the limitation of less control in structure shapes and sizes at micrometer scale. The problems are mainly the relatively long wavelengths of the visible light, the shadowing effects, and the non-uniformity in chemical reactions. These problems can be avoided by employing the state of the art lithographic ion milling technique in combination with micromachining technique. The ion milling is used to accurately define the patterned structures on micrometer scales by removing unmasked areas. The quality of the resulted structures is primarily determined by the quality of the photoresist masking developed before ion milling. To further increase the accuracy in the masking, X-ray lithography may be employed, since these sources have much shorter wavelengths than the visible light, thus they create sharper structures. X-ray micromachining can also be used to directly construct the desirable micron-sized structures once the required layering structures are fabricated in thin film forms by magnetron sputtering. Ion milling and X-ray lithography can also be used in creating corrosion media consisting of arrays of closely spaced nano-sized magnetic dots or strips.

A packaged, multipurpose micro-sensor is provided by one embodiment of the present invention for characterizing the corrosion-causing variables and, e.g., the extent of atmospheric corrosion damage taking place on a given structure at a given location, especially in a coastal or industrial region and the regional influence on the corrosion rate. These sensors can also be used for application in energy producing systems. The sensor may also be used to electrochemically study any liquid and determine characteristics of its composition. Biological sensors, e.g., bacterial action and/or biological media composition may also be provided. One particular type of application is an enzyme-linked sensor in which a specific analyte, which itself may have small or insignificant corrosive properties, is responsible for producing a corrosive effect corresponding to a concentration of the analyte, e.g., concentration of glucose in blood.

Thus, for example, a sensor may be provided with a spin valve sensor which is coated with a trapped or immobilized glucose oxidase, Glucose oxidase (β-D-glucose:oxygen 1-oxidoreductase, EC1.1.3.4) catalyses the oxidation of β-D-glucose to D-glucono-1,5-lactone and hydrogen peroxide, using molecular oxygen as the electron acceptor. Hydrogen peroxide solutions, especially at basic pH, is more corrosive than oxygen dissolved in water, and thus a differential effect is anticipated based on the glucose concentration.

The present invention is advantageous because:
1) It is surface sensitive at atomic scale allowing ultrasensitive characterization and measurement of corrosion and chemical reactions, as well as reversible and irreversible chemical influences.

2) It allows easy integration with microelectronic circuits and communication board to make compact and remote all-electronic sensing unit.
3) It is amenable to efficient manufacturing processes, to be made into a self supporting chip or as embedded active component in structure materials.
4) It provides reliable measurement of corrosion rate and high selectivity in identifying chemical reaction and agents.
5) It has an ultra short electronic response time (nanoseconds) to provide rapid diagnosis and realtime monitoring of multiple sensing matrix.
6) It permits a simple sample structure and low manufacturing costs with compatible fabrication methods with the existing electronic technology.
7) It permits incorporation of multifunctionality in sensing and decision making systems.

It is therefore an object of the invention to provide an environmental condition sensor within an electronic device, comprising an environmentally exposed metal sensing portion sensitive to environmental exposure, in proximity to a component of the electronic device sensitive to a corresponding environmental exposure; a circuit for determining a response of the exposed metal sensing portion to the environment; and an output presenting a signal corresponding to the environmental exposure. The exposed metal sensing portion generally corrodes or otherwise responds in response to environmental exposure. The exposed metal sensing portion may produce an instantaneous response or cumulative response to environmental exposure. The exposed metal sensing portion may be provided within a package having leads, for example a surface mount package compatible with pick-and-place equipment compatible with modern high speed board assembly systems. The exposed metal sensing portion preferably has an environmental response which models an environmental response of the component, and thus predicts or models a failure or other response thereof. The exposed metal sensing portion is preferably part of a giant magnetoresistive (GMR) effect device, wherein the circuit sensing one or more properties of the GRM effect device selected from the group consisting of: (i) the lower switching field and the higher switching field of the spin valve; (ii) an electrical resistance of the spin valve, and (iii) the giant magnetoresistive value of the spin value. Other sensing schemes are also possible.

It is also an object of the invention to provide an electrical sensor, comprising a spin valve comprising a giant magnetoresistive effect structure having a first magnetic layer and a second magnetic layer, the first and second magnetic layers being separated by a thin non-magnetic layer, wherein at least one of the first and second magnetic layers is chemically exposed to an environment, at least one of, e.g.,: (a) the lower switching field and the higher switching field of the spin valve; (b) an electrical resistance of the spin valve, and (c) the giant magnetoresistive value of the spin value, are dependent on at least one chemical property of the environment or an interaction with the environment. The sensor system may also include a device for reading the change in property of the GMR effect structure, for example to read the electrical resistance of the spin valve. The chemical properties may include a corrosive tendency, the magneto-electronic sensor sensing at least one of a corrosive potential of the environment and a corrosion of elements exposed to the environment. At least one of the first an second magnetic layers may comprise a metal, wherein the environment oxidizes the metal to alter a magnetic property thereof, to thereby alter an interaction of the first magnetic layer with the second magnetic layer.

The sensor is not limited to detection of corrosion or permanent metal oxidation, and, for example, the chemical properties may comprise an analyte in the environment, the sensor responding by producing an instantaneous, time weighted, and/or cumulative output relating to exposure to the analyte. Advantageously, according to one embodiment, the analyte interacts with an enzyme, the enzyme generating a chemical species which interacts with at least one of the first and second magnetic layers. Preferably, the exposed metal layer is nano-textured, to alter and/or control a chemical reaction rate, for example speeding it up by increasing an exposed surface area. The sensor may be used as part of a control system, for example to normalize the corrosion potential of the environment, or to influence an anti-corrosive process. A control system may also depend on presence of an analyte without corrosive effects.

BRIEF DESCRIPTION OF THE DRAWINGS

For a further understanding of the nature, objects, and advantages of the present invention, reference should be had to the following detailed description, read in conjunction with the following drawings, wherein.

DETAILED DESCRIPTION OF THE PREFERRED EMBODIMENTS

Figure 1A:
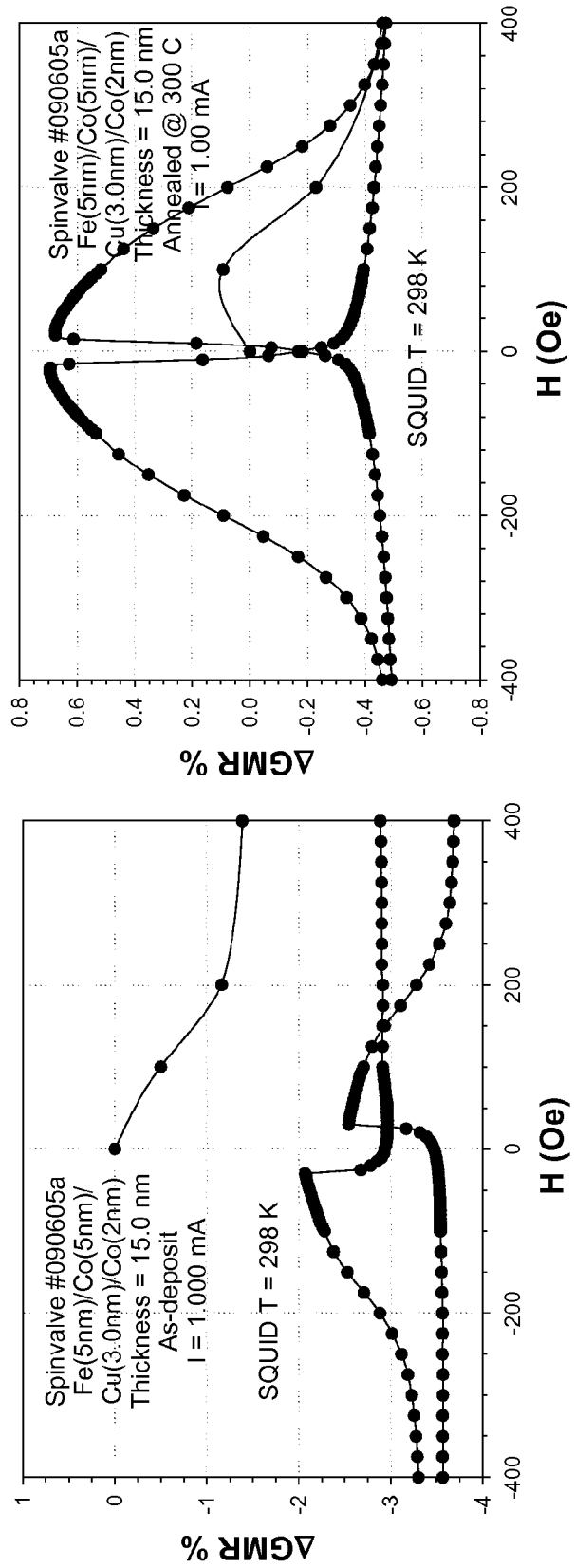
FIGS. 1A, 1B and 1C show the effect of different annealing temperature on GMR values and high switching field.

This invention utilizes combined property of corrosion protection and controlled chemical reaction rates for a Cobalt (Co) top layer in a magnetic spin valve. The degree of chemical reaction is monitored by measuring the changes in magnetic property of the top Co layer, which is very sensitive to the occurrence of corrosion and chemical reaction. It has been demonstrated that the magnetic property of a thin Co layer to chemical reaction at the atomic scale can be easily quantitatively measured using spin valves as a sensing unit. The most noticeable magnetic property change that is affected by corrosion and chemical reaction is the magnetic switching field in a small applied magnetic field. The change in switching field can be easily measured using a spin valve with GMR effect with Co as the top magnetic layer.

To achieve ultra-high sensitivity, the corrosive-condition sensitive media in the sensors is preferably in the form of nano-structured magnetic materials such as patterned arrays, nano-scaled granular thin films, or magnetic ion loaded mesoporous media. There are four important reasons for choosing nano-scaled materials for corrosion testing, based on geometrical, structural and magnetic considerations:

1) The very small feature sizes of the corrosion media will enhance the sensitivity of the sensors due to a comparable length scale to the corrosion thickness. For example, the thickness of oxide layers formed on ferromagnetic metals is usually several nanometers (after several days of exposure), comparable to the characteristic sizes of nano-structured materials. Due to very small size of the corroding objects the sensitivity of the sensor will be greatly enhanced because a large part of the material can be corroded in a short time.

2) A related property of the nano-sized and porous materials is their large surface to volume ratio, which can be orders of magnitude higher than for conventional polycrystalline alloys. The corrosion rate and the usable exposure time in corrosion testing can be controlled by varying the characteristic size of the corroding objects, tailored to have suitable sensor response for different materials. The corrosion rates for bulk Fe, Ni and their alloys are typically in the range of 2 to 500 nm/hour, while that for Co is lower. The corrosion rates of nano-structured materials can be hundreds times higher than that of the bulk materials.

3) The microstructure of these materials is well defined upon reaching nanometer scales. Corrosion of very fine objects with uniform sizes (i.e. grain or pattern size) and well defined crystallographic orientations is expected to be highly repeatable for a given corrosive environment. Because of specific structure of these materials the stress corrosion and pitting corrosion mechanisms can be neglected.

4) Magnetic grains with dimensions below 150 nm can be single domain. They have simple inner magnetic structure, which makes the interpretation of the magnetic behavior much simplified comparing to larger grains where domain wall movements should be taken into account. The magnetic behavior of single domain magnetic grains has been thoroughly studied and understood. For example, the domain magnetization re-orientation is considered to be a coherent rotation. The dependence of the magnetization on the grain size has been well established.

There are many magnetic properties of nano-structured magnetic materials, which are suitable for use in corrosion testing. The most relevant properties are:

1) Magnetization—The saturation magnetization should decrease, approximately proportional to the mass of corroded magnetic material. Some deviations from this relation are expected only for very thin films (of the order of several atomic layers) or for very small isolated particles. The decrease in the magnetization for ultra-fine particles, with the particle size, is more pronounced due to superparamagnetism and particle surface effect. The saturation magnetization can be measured using highly sensitive magnetic field sensors to monitor corrosion-related changes. The magnetic field sensor is preferably a GMR spin-valve, although a spin-tunneling device or Magnetic Hall effect device might also be used.

2) Initial permeability—The inductive sensing of dynamic permeability can be applied to measure permeability, which is sensitive to magnetic anisotropy. It was demonstrated that increasing the distances between nano-crystalline grains results in a dramatic change in magnetic properties. The advantage of the inductive method is that it is a noncontact method, hence, the testing material can be easily replaced. It is also important that this method works in a wide temperature range, so both low temperature and high temperature corrosion can be monitored. Special interests lie in measuring small ferromagnetic particles, which demonstrate superparamagnetic behavior at the ambient temperature. This may be the case for mesoporous media or thin film alloys containing ferromagnetic particles. Corrosion of such materials will decrease the grain size of the ferromagnetic particles, lowering their blocking temperature. The consequence is a rapid decrease in the permeability at the onset of corrosion.

The spin valve has a simple structure of Co/Cu/Co with a proper buffer layer (e.g. Fe) on a substrate (Si or glass). The top and bottom magnetic layers respond to applied magnetic field differently due to different response property, layer thickness, and chemical environment. The spin valve possesses unique property of having different resistance values with different magnetic configuration of the two Co layers: The magneto-electronic response curve sensitively depends on the relative magnetic orientation of the two magnetic layers, with the resistance having a higher value when two magnetic vectors are in opposite direction. Thus, such spin valves provide a practical means to measure the magnetic orientation of individual layers. Since the magnetic responses critically depend on the chemical environment and reaction, this provides a sensitive method of determining the degree of corrosion and chemical reaction, and allows implementation of an integrated all-electronic sensor and circuit. It is also possible to build remotely monitored unit by incorporating wireless data communication.

The spin valve sensor according to the present invention is generally compatible with various semiconductor processing techniques, and thus the sensor may be provided on the same substrate or integrated with processing circuitry and other circuitry.

Figure 1B:
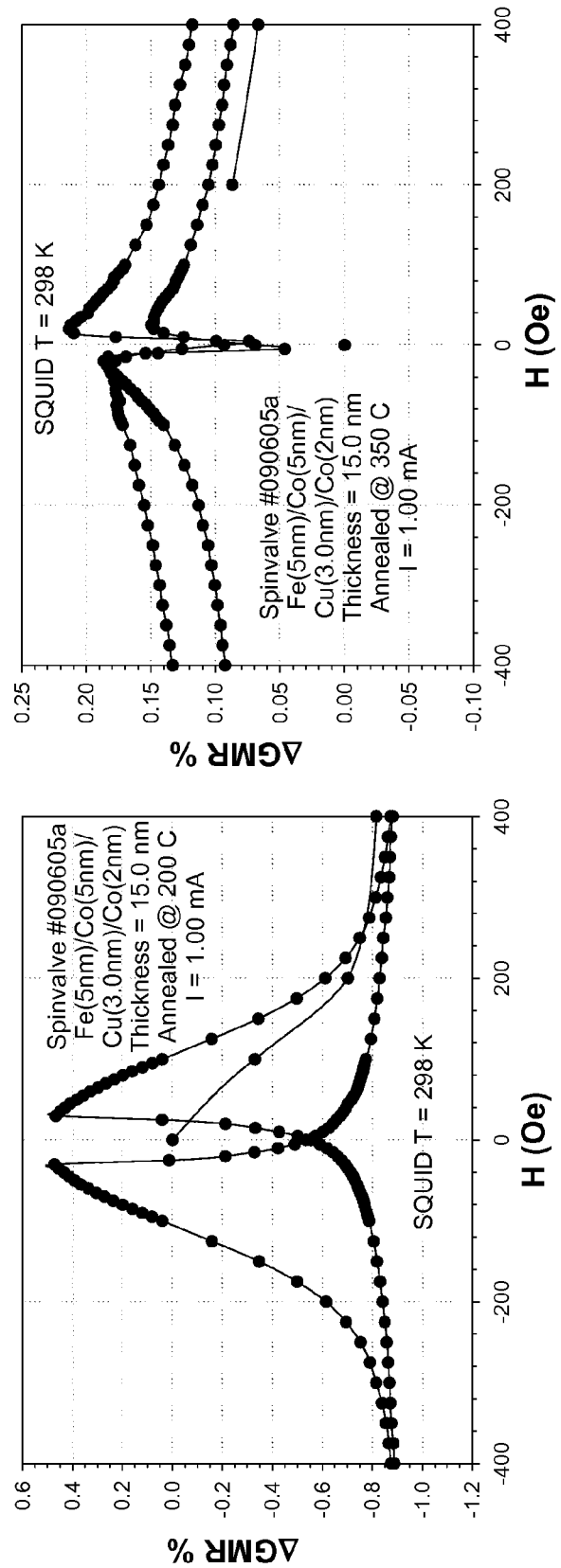
Figure 1C:
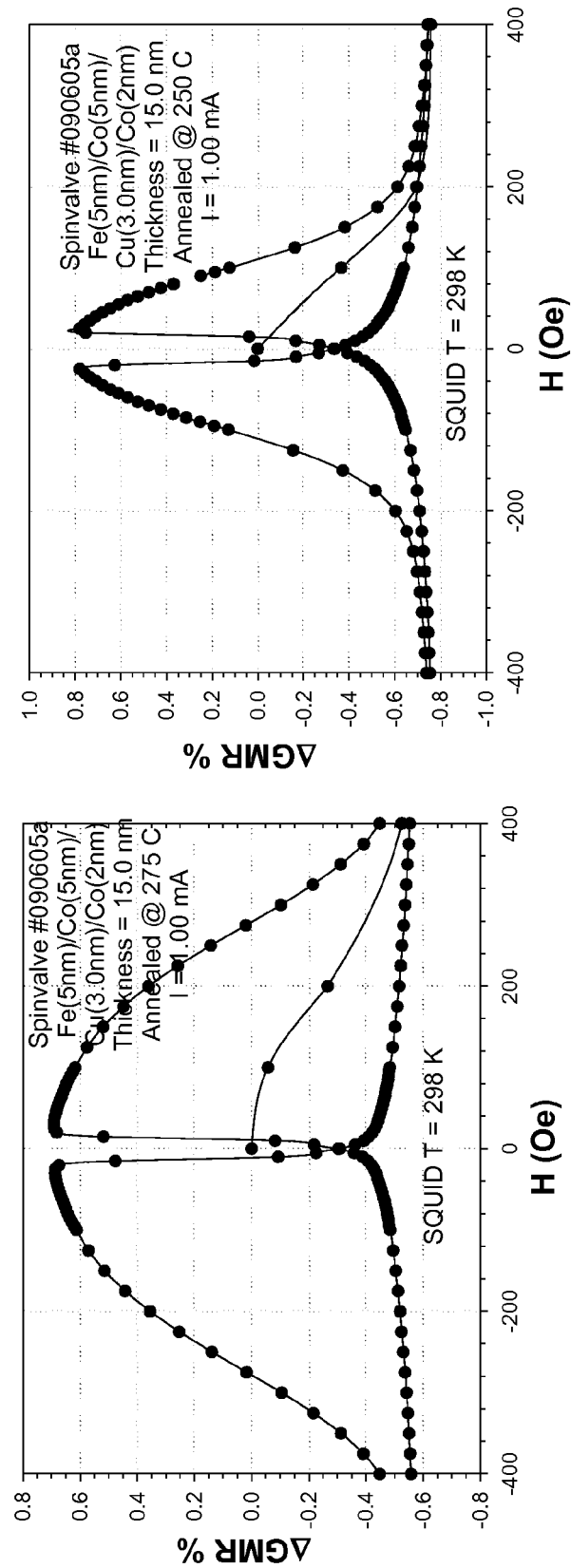
Figure 2A:
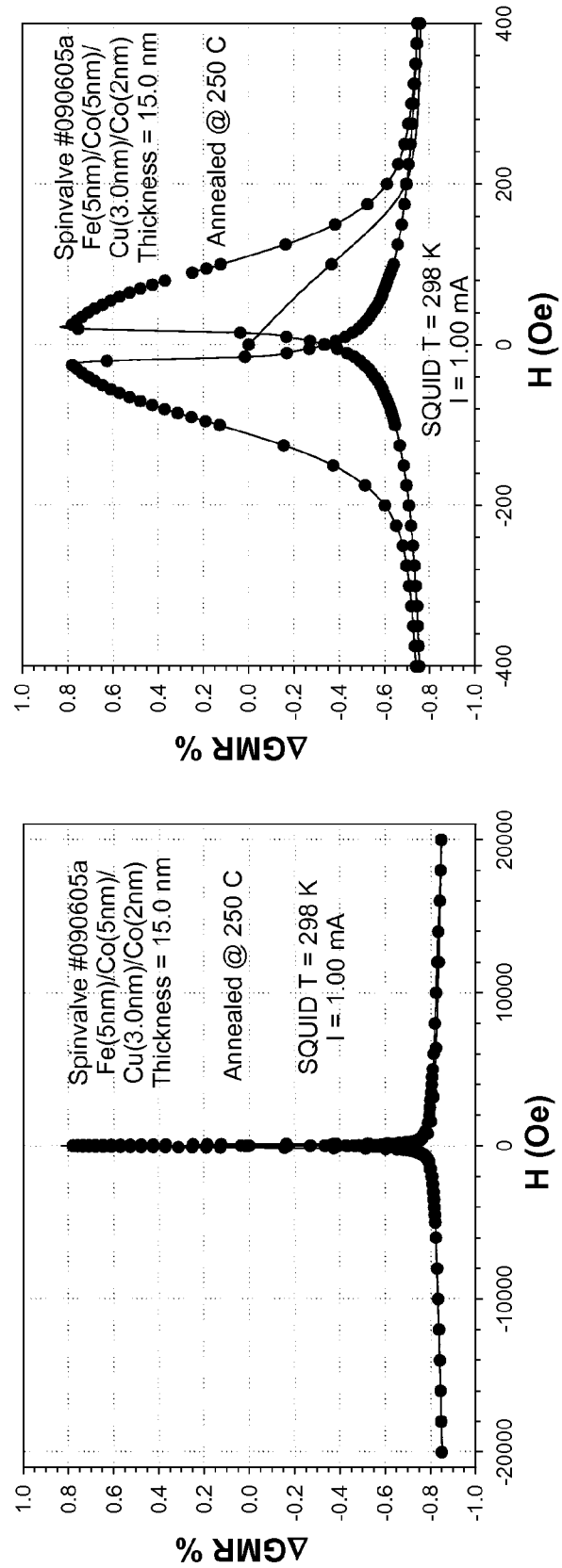
FIGS. 2A, 2B, 2C, 3A, 3B and 3C show the effect of chemical environment on GMR response of a GMR sensor, before an after immersion in de-ionized water for 10 minutes, respectively
Figure 2B:
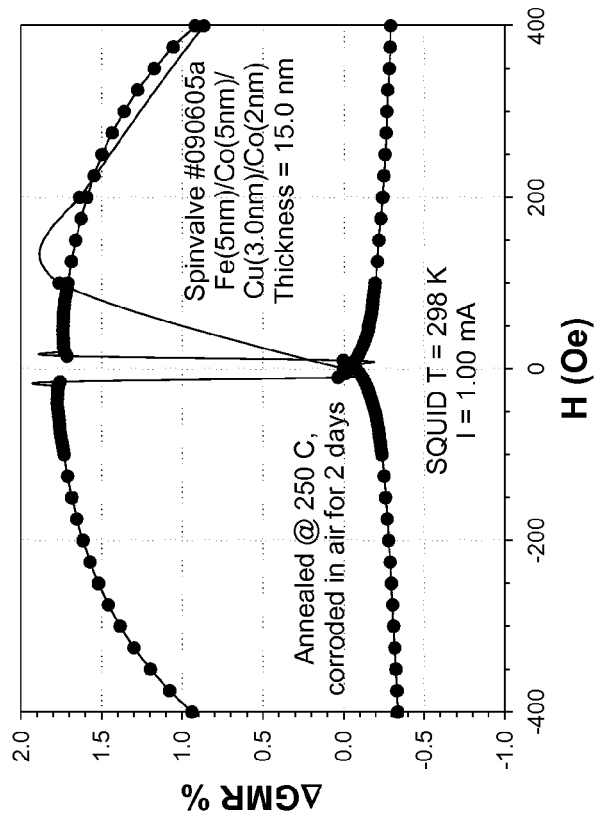
Figure 2B:
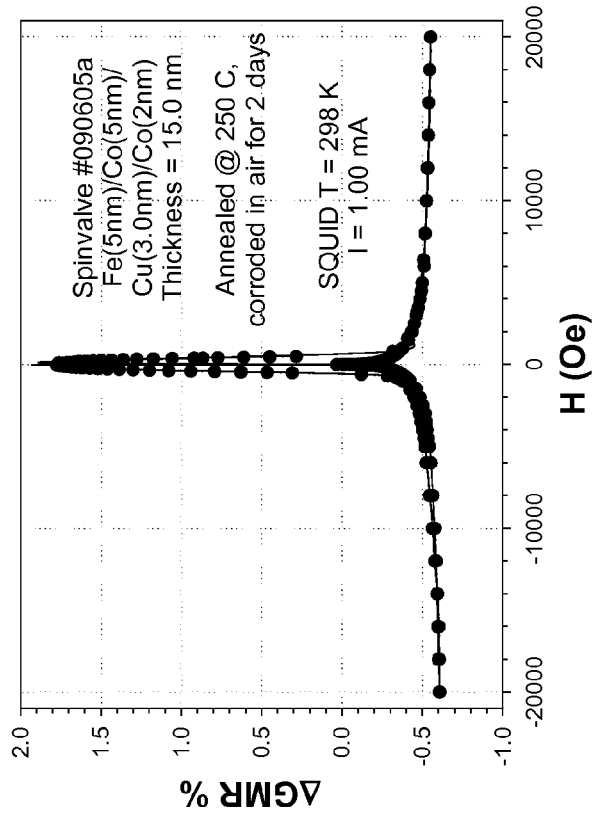
Figure 2C:
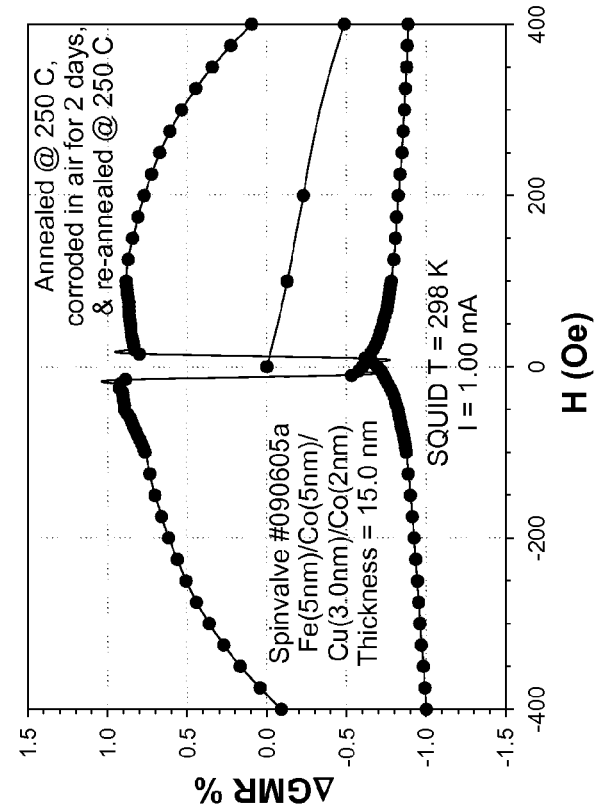
Figure 2C:
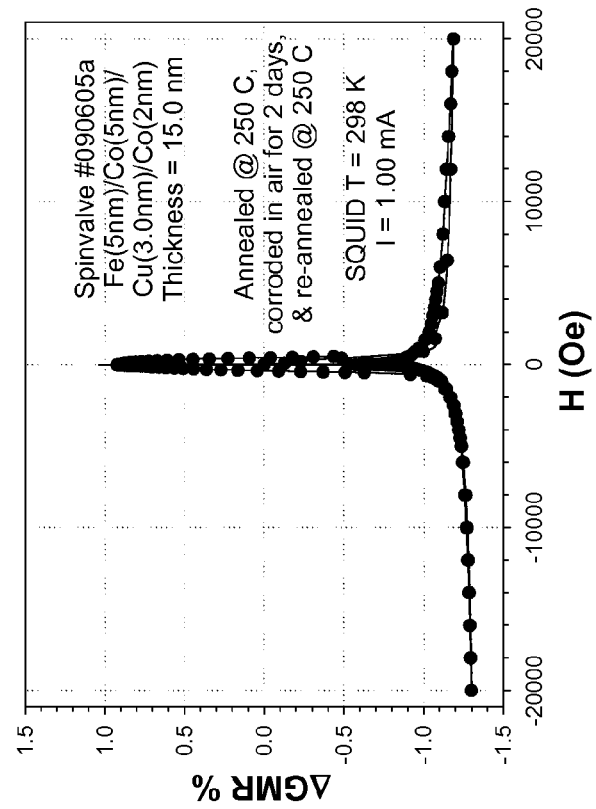

The magneto-electronic properly of spin valves can be modified by applying thermal annealing up to 350° C. FIG. 1 shows the typical magnetoelectronic response curve of a series of Co/Cu/Co/Fe spin valves annealed at different temperatures ranging from 200° C. to 350° C.

According to one embodiment of the invention, the spin valve design has a layering configuration of Co (2 nm), Cu (3 nm), Co (5 nm), and Fe (5 nm). The spin valve films were deposited in a high vacuum system with a base pressure better than $1.5 \times 10^{-7}$ torr. The film deposition was done using magnetron sputtering with elemental targets and deposition rates of about 0.2 nm/s. The deposition Ar pressure was kept at about 4.0 mTorr. The annealing at various temperatures was done in a following reducing gas of composition H8.5%-Ar for 30 minutes or more. Proper ramping was allowed in the annealing procedure.

These spin valves have a GMR value of about 1 to 10%, and a lower switching field of about 20 Oe, which corresponds to the magnetic switching of the lower Co/Fe bi-layer. The higher switching field is highly dependent on the annealing temperature. As shown in FIG. 1, annealing temperature has a strong effect on the GMR values and high switching field.

Initially, annealing at lower temperatures (below 250° C.), the GMR values remains unchanged, while the higher switching field is reduced slightly from about 150 Oe to 120 Oe. Subsequently, the GMR value is slightly enhanced and the higher switching field is increased (to about 220 Oe). Upon annealing at 350° C., this particular spin valve lost its GMR response.

Figure 3A:
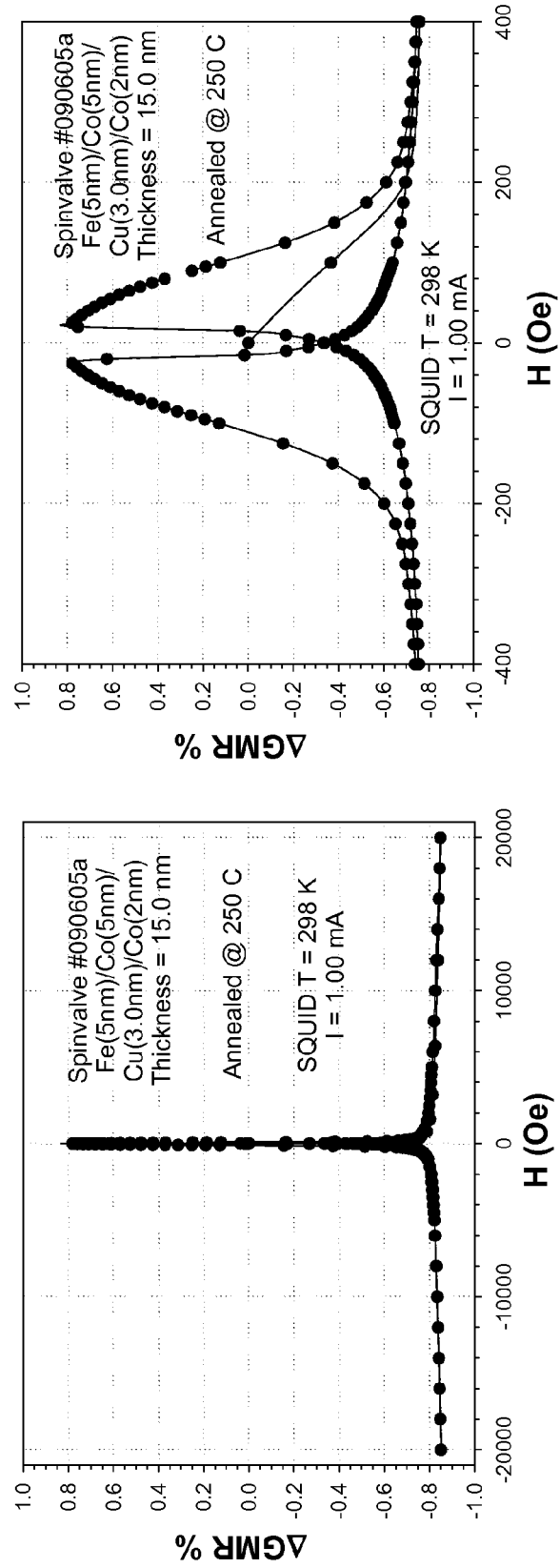
Figure 3B:
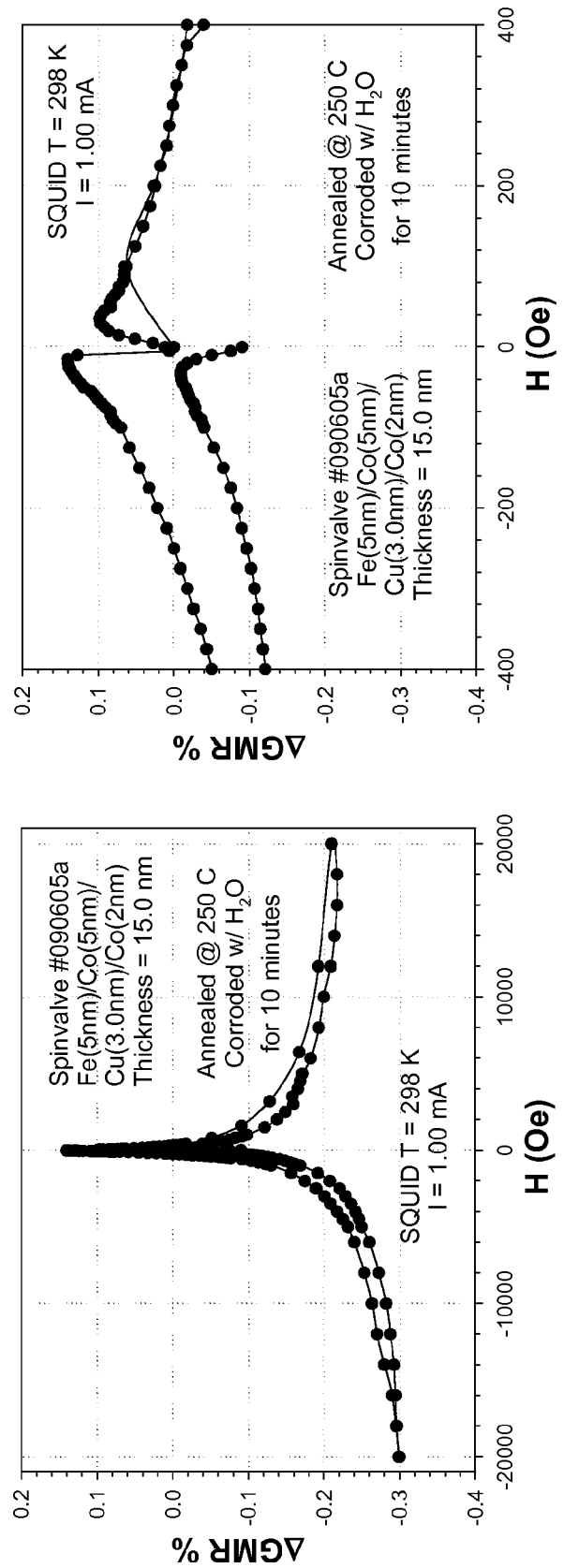
Figure 3C:
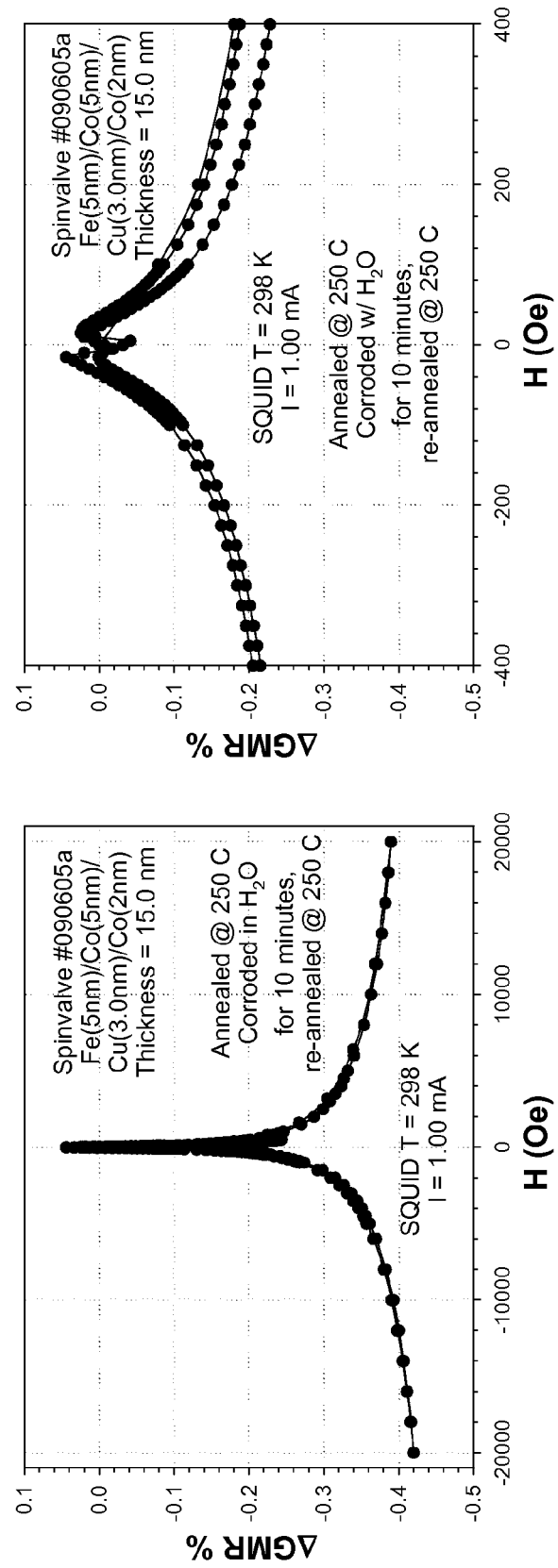

FIGS. 2 and 3 show the influence of chemical environment on the GMR response. This spin valve was annealed at 250° C. before subject to chemical sensing tests. After being corroded in air for two days, the GMR value is increased by 20% (from 1.6% to 2.0%), and the high switching field was increased dramatically from 80 Oe to 4200*e* (FIG. 2). Upon further annealing, the high switching is somewhat reduced. The same spin valve film, after submerged in dionized water for 10 minutes or less, lost its GMR response altogether (FIG. 3). This demonstrates the dramatic sensitivity of such spin valves to the chemical reaction and its selectivity.

The materials for corrosion testing are initially produced in the form of thin magnetic films of Fe, Co and Ni (or other magnetic alloys or compounds) with thickness values ranging from 100 nm to 2 μm, although thinner films, e.g., 10-200 nm, may be used. The thin films may be formed using magnetron sputtering deposition. Magnetron sputtering is a versatile technique that allows production of a large variety of thin films with repeatable microstructures (epitaxial or polycrystalline films) and compositions. Nano-sized arrays and micron-sized device structures may be patterned from these films using X-ray lithography and ion milling. Granular nanocrystalline films can be produced either by the magnetron sputtering deposition or using a laser ablation deposition.

The MCM-41 mesoporous media can be made by chemical methods in known manner. MCM-41 has hexagonal arrays of micellar rods, which are used as templates for silicon oxide growth and after removing the organic medium by calcination they form an array of tubes with diameters of 2 to 10 nm. These tubes can be loaded by ferromagnetic materials and used as a corrosion media.

The new composite corrosion sensors are based on the vitality of most magnetic materials with reactive chemical species and ultra-sensitivity of the magnetic field sensors made from specially structured and selected layered or composite magnetic systems. The spin-valve and spin-tunneling devices all have maximum sensitivity in current-perpendicular-to-plane configuration. Since the thickness of these magnetic structures is generally in the range of several to tens nanometers, to achieve reasonably detectable signals the lateral dimensions need to be in the micrometer range. Also, to induce substantial magnetic fields at the field sensors, the corrosion media will be required to reach micrometer sizes. The micrometer and submicrometer dimensions may be achieved by photolithography in combination with ion milling and micromachining using hard X-ray.

One consideration is whether the magnetic field sensors are sensitive and stable enough to detect the slight variation in magnetic field produced by the magnetic corrosion media during the course of monitoring corrosive environments. Let us assume that Fe or Co particles are used as corrosion agents that fill a porous medium with 50% of the total volume. Alternatively, one considers patterned arrays of magnetic strips or dots with 50% magnetic volume. We also assume that all the magnetic particles are magnetized along the same orientation. The magnetic field, B generated by these particles at a distance of R from the surface of the magnetic medium is found to be $B = P(4\pi M)(R/L)\ln(I + t/R)$. In this expression, t is the thickness and L the lateral dimension of the overall magnetic medium, M the magnetization density of the magnetic component, and P the magnetic volume percentage.

For bulk Fe and Co, $(4\pi M) = 2.2$ and 1.8 Tesla, respectively, thus, on the average we have $4\pi M = 2$ Tesla. For nano-sized magnetic particles it is known that the Curie temperature decreases substantially as compared with the bulk value. There is a large reduction in the saturation magnetization at the ambient temperature. For example, it has been found that for Fe particles with their sizes ranging from 2 to 6 nm the M value at the ambient temperature is reduced by 40% compared to the bulk value. Thus, the realistic value for $(4\pi M)$ should be somewhat smaller. Let us further assume that it is 60% of the bulk value, and that the thickness, t, of the magnetic medium equals the distance, R, from the surface. The practical limit for the lateral dimensions of micro-sized structures by micromachining is about 10 micrometers. If we assume a L/R ratio of 10 (about 1 micrometer thick magnetic film), the estimated magnetic field for the magnetized medium is about 690 Gauss, for 50% magnetic volume fraction. This field is strong enough to be easily detected by GMR sensing devices. When one atomic layer on the magnetic particle surfaces is fully corroded the change in the overall magnetization can be as large as 30% due to a large surface area. This corresponds to a field variation of 210 Gauss.

For the case of magnetization parallel to the medium plane, the induced magnetic field is reduced further by a factor of about 0.2. The total induced field and its variation for one atomic layer corrosion correspond to, respectively, 140 and 40 Gauss. These values can be further enhanced by decreasing the lateral dimensions of the magnetic corrosion media and by positioning the field sensors closer to the corrosion media. The fact that the magnetic media consist of cluster arrays instead of uniformly dispersed magnetic atoms further increases the local fields. The parallel magnetization configuration is required for spin valve and spin-tunneling magnetic field-sensing configuration since the easy axis of the magnetization for the sensor structure is in plane. These structures are the most sensitive field-sensing devices known to date, ideally suited for the parallel magnetization configuration. The best demonstrated spin-valve sensors have a field sensitivity of 3%/Gauss. Such sensitivity limits are well suited for accurate determination of these field variations.

Exchange biased GMR spin valves are a preferred sensor type. The direction of the magnetization of one magnetic layer is pinned by the exchange biasing to a contiguous antiferromagnetic layer, while that of the other magnetic layer is free to rotate and thus probe the magnetic field. Specific systems include permalloy/Cu and Co/Cu spin-valves using FeMn and NiO as the antiferromagnetic pinning layers. Magnetron sputtering has been shown to be one of the best deposition methods to grow spin-valve structures.

The magnetic structures or thin films for sensing magnetic fields are deposited on Si wafers, and then patterned according to predefined geometry and dimensions, by combined lithography, ion milling, and micromachining After being patterned into field sensing devices, the structures are embedded in a non-magnetic and non-conductive protective medium such as $SiO_2$. The resulting assembly is then polished, reactively ion etched and annealed to produce a smooth surface. Annealing also serves to modify the internal microstructures of the field-sensing structures for improved performance. Further fabrication of desirable corrosion thin films suitable for specific corrosive environments is then done on the treated surface. The new film is patterned into micrometer sizes, and nano-sized structures of strip or dot arrays are fabricated on the patterned corrosion medium to enhance the exposure area. After patterning, the sample is placed in a high vacuum chamber to be ion etched to remove the oxide layers to expose the magnetic surfaces. Then, an intermediate porous corrosion-damping layer, such as porous $SiO_2$ can be deposited to modify the corrosion rate of the medium. Another protective capping layer can be deposited to prevent corrosion before testing and/or use.

The approach of directly fabricating the corrosion medium on a protective spacer on the field-sensing structure is desirable due to minimized intermediate processes and the need to expose the corrosion medium to testing or corrosive environments to be analyzed. The present invention provides a method for integrating the two separate processes of making the field-sensing device layer and magnetic corrosion layer into a single process.

In case that the corrosion medium is fabricated separately, such as by wet chemical methods, slices of the fabricated corrosion medium are bonded onto the magnetic-field sensing structures. According to the formulation provided above, an acceptable geometrical configuration is with a comparable thickness of the corrosion medium to the distance of the field-sensing structure to the medium. The sensitivity will be otherwise affected in two aspects. For too thick a corrosion medium, the effective corrosion will tends to be in the surface region. The effectiveness of inducing significant field change is minimized and difficult to control. For a thin corrosion medium the induced field effect is too weak to be effective. Reactive ion etching is employed to remove undesirable materials to modify the corrosion layer thickness once the two components are bonded together, to achieve optimal performance. After desirable thickness is achieved a protective cap layer is deposited.

Corrosion starts and mostly occurs on the surface within a layer with a typical thickness of 2 to 10 nm. In regular magnetic recording media with thick magnetic films, there is little correlation between the topography and the magnetic domain structure as determined by SPM: because the latter is a bulk effect whereas the former is a surface effect. For nano-scaled magnetic corrosion media, there should be a correlation between the changes in the magnetic domain structure and the topography variation by corrosion, since in such systems the magnetic film thickness is comparable to corrosion product layer thickness. For relative corrosive materials such as Ni, Fe, and their alloys, gas phase exposure to corrosive species (with different electric negativities) under controlled temperature, concentration and flow conditions can be sensed. Factors affecting corrosion rates include temperature, humidity, gas content and flow rates. Chlorine and hydrogen ions are known strong corrosive agents, while oxygen is relatively weaker. For corrosion resistive Co and its alloys, the sensor may be suitable for analyzing both gaseous and aqueous environments.

Magnetron sputtering deposition is utilized to fabricate magnetic thin films for both corrosion media and magnetic field-sensing structures. The process is controlled to achieve controlled material properties, such as crystalline orientation, surface smoothness, interface quality, film adhesion, and their dependence on deposition conditions. The film systems for corrosion media may include thin films of one or more of Ni, Co, Fe, Gd, etc., and their magnetic granular alloys with other non-magnetic elements. For comparison with the resulting corrosion products, the corresponding magnetic-oxide and sulfate films may be fabricated and studied. Magnetic thin films and multilayers for field sensing devices may include giant moment magnetic films, such as Fe—Pt, GMR spin-valve structures (e.g. FeNi/Cu/FeNi/MnFe), and spin-tunneling structures.

The individual processes in the production of a preferred sensor, in sequential order, are:

1) The field-sensitive thin film structures deposited on Si wafers, followed by property measurement and characterization.
2) The field-sensitive structures processed into micron-sized devices including proper signal readouts.
3) Buffer layer deposited on the devices followed by reactive ion etching to gain desirable thickness and a smooth surface.
4) Magnetic corrosive films deposited on the buffer layer, followed by patterning into micron-sized structure.
5) For mesoporous medium containing magnetic particles, thin slices will be bonded to the buffer layer, thinned down by reactive ion etching to desirable thickness, and patterned into micron-sized dimensions.
6) To enhance surface area for the films the corrosion media fabricated into nano-scaled structures.
7) Corrosion rate modification realized by introducing an intermediate porous layer.
8) Protective cap layer deposited.

There has thus been shown and described a sensor and sensing method which fulfill all the objects and advantages sought therefor. Many changes, modifications, variations and other uses and applications of the subject invention will, however, become apparent to those skilled in the art after considering this specification and the accompanying drawings which disclose the preferred embodiments thereof all such changes, modifications, variations and other uses and applications which do not depart from the spirit and scope of the invention are deemed to be covered by the invention, which is to be limited only by the claims which follow.

BIBLIOGRAPHY

1. N. D. Tomashov, in Theory of Corrosion and Protection of Metals, ed. B. H. Tytell, I. Geld, H. S. Preisner, (Mac- Millan, New York, 1966), p. 80-105, 502-523, 604-612, 367-398, 435-438, 459-461, 284-6, 32.
2. C. Leygraf, "Chp. 12, Atmospheric Corrosion"; F. P. Fehlner and M. J. Graham, "Chp. 4, Thin Oxide Film Formation on Metals"; B. MacDougall and M. J. Graham, "Chp. 5, Growth and StabiFty of Passive Films"; D. Thierry and W. Sand, "Chp. 13, Microbially Influenced Corrosion"; R. C. Newman, "Chp. 10. Stress-Corrosion Cracking Mechanisms"; H.-H. Strebnow, "Chp. 7, Mechanisms of Pitting Corrosion", in Passivity Corrosion Mechanisms in Theory and Practice, ed. P. Marcus and J. Oudar, (Mercel Dekker, New York, 1995).
3. H. H. Uhlig, in Corrosion and Corrosion Control, (John Willey & Sons, New York, 1971).
4. D. Van Rooyen and H. R. Copson, "Atmospheric Corrosion of Some Nickel Alloys", p. 175-186; C. W. Briggs, "Atmospheric Corrosion of Carbon and Low Alloy Cast Steels", p. 271-284, in Metal Corrosion in the Atmosphere, (American Society for Testing and Materials, Baltimore, 1968).
5. J. M. West, in Basic Corrosion and Oxidation, (Ellis Hormwood, Chichester 1980).
6. A. Aharoni, in Introduction to the Theory of Ferromagnetism, (Clarendon Press, Oxford, 1996).
7. D. Jiles, in Introduction to Magnetism and Magnetic Materials, (Chapman & Hall, London, 1991).
8. M. G. Fontana, in Corrosion Engineering, eds. R. Gibala, M. Tirrell and C. Wert, (McGraw-Hill, New York, 1986), p. 109-142, 63-73, and 172.
9. C. T. Kresge, M. E. Leonowicz, W. J. Roth, J. C. Vartuli & J. S. Beck, "Ordered Mesoporous Molecular Sieves Synthesized by Liquid-Crystal Template Mechanism", Nature, 359, (1994) 710.
10. G. Herzer, "Grain Size Dependence of Coercivity and Permeability in Nanocrystalline Ferromagnets", IEEE Trans. on Magn. 265, (1990) 1397.
11. A. Slawska-Waniewska, L. Malkinski and M. Kuzminski, "On the Role of Magnetic Coupling between Crystalline Grains in Nanocrystalline Alloys", IEEE Trans. On Magn. 335, (1997) 3727.
12. M. Prutton, in Thin Ferromagnetic Films, (Butterwoth & Co., London, 1964), p. 74-78, 93-1 13, and 197-223.
13. H. Zijlstra, in Selected Topics in Solid State Physics (vol. 9): Experimental Methods in Magnetism, 11, ed. E. P. Wohlfarth, (North Holland, Amsterdam, 1967), p. 103-140.
14. W. F. Brown, in Selected Topics in Solid State Physics (vol. 1): Magnetostatic Principles in Ferromagnetism, ed. E. P. Wohlfarth, (North Holland, Amsterdam, 1962), p. 83-85.
15. M. N. Baibich, J. M. Broto, A. Fert, F. Nguyen van Dau, F. Petroff, P. Etienne, G. Creuzet, A. Friederich and J. Chazeles, "Giant Magnetoresistance of (OOl)Fe/(OOl)Cr Magnetic Superlattices", Phys. Rev. Lett., 61, (1988) 2472.
15. R. L. White, "Giant Magnetoresistance: a Primer", IEEE Trans. Magn., 28, (1992) 2482.
16. S. S. P. Parkin, Z. G. Li and D. J. Smith, "Giant Magnetoresistance in Antiferromagnetic CoICu Multilayers", Appl. Phys. Lett., 58, (1991) 2710.
18. J. S. Moodera, L. R. Kinder, T. M. Wong and R. Meservey, "Large Magnetoresistance at Room Temperature in Ferromagnetic Thin Film Tunnel Junctions", Phys. Rev. Lett., 74, (1995) 3273.
19. T. Miyazaki and N. Tezuka, "Giant Magnetic Tunneling Effect in Fe/Al2O3/Fe Junction", J. Magn. Map. Mater., 139, (1995) L23 1.
20. M. Julliere, "Tunneling Between Ferromagnetic Films", Phys. Lett., 54, (19 75) 225.
21. J. C. Slonczewski, "Conductance and Exchange Coupling of Two Ferromagnets Separated by a Tunneling Barrier", Phys. Rev. B, 39, (1989) 6995.
22. C. L. Canedy, G. Q. Gong, J. Q. Wang, and G. Xiao, "Large Magnetic Hall Effect and Enhanced Magnetic Moment in Fe—Pt Thin Films", J. Appl. Phys. 79, (1996) 6126.
23. R. S. Popovic, in Hall Effect Devices, (Adam Hilger, New York, 1991).
24. J. Q. Wang and G. Xiao, "Transition-Metal Granular Solids: Microstructure, Magnetic Properties, and Giant Magnetoresistance", Phys. Rev. B 49, (1994) 3982.
25. W. D. Wang, F. G. Zhu, W. Y. Lai, J.-Q. Wang, Z. Zhang, "Microstructure, Magnetic Properties and Giant Magnetoresistance of Granular Cu—Co Alloy", submitted to Phys. Rev. B.
26. J.-Q. Wang, R. C. Barker, G.-J. Cui, T. Tamagawa, B. H. Halpern, "Doped Rare Earth Perovskite Mn Films with Colossal Magnetoresistance", Appl. Phys. Lett. 71, 3418 (1997).
27. J.-Q. Wang, N. D. Rizzo, D. E. Prober, L. R. Motowidlo, B. A. Zeitlin, "Flux Pinning in Multifilamentary Superconducting Wires with Ferromagnetic Artificial Pinning Centers", IEEE Trans. Appl. Supercond. 7, 1130 (1997).
28. J. D. McCambridge, N. D. Rizzo, J.-Q. Wang, X. S. Ling, D. E. Prober, L. R. Motowidlo, B. A. Zeitlin, "Critical Current Density in NbTi/Nb and NbTiTi Multilayers", IEEE Trans. Appl. Supercond. 7, 1 134 (1997).
29. N. D. Rizzo, J.-Q. Wang, D. E. Prober, L. R. Motowidlo, and B. A. Zeitlin, "Ferromagnetic Artificial Pinning Centers in Superconducting $Nb_{36}Ti_{64}$ Wires", Appl. Phys. Lett. 69, 2285 (1996).
30. J.-Q. Wang and G. Xiao, "Finite Size Effect and Temperature Dependence of Giant Magnetoresistance in Magnetic Granular Materials", J. Appl. Phys. 79, 5587 (1996).
31. C. L. Canedy, J.-Q. Wang, and G. Xiao, "Large Magnetic Hall Effect and Enhanced Magnetic Moment in Fe—Pt Thin Films", J. Appl. Phys. 79, 6126 (1996).
32. J.-Q. Wang, N. D. Rizzo, J. D. McCambridge, D. E. Prober, L. R. Motowidlo, and B. A. Zeitlin, "Ferromagnetic Artificial Pinning Centers in Multifilamentary Superconducting Wires", Adv. Cryo. Eng. 42 (1995).
33. G. M. Ozeryansky, D. R. Dietderich, N. D. Rizzo, J.-Q. Wang, D. E. Prober, and L. R. Motowidlo, "Fabrication and Properties of Nb3Sn Conductor with APC Structure", Adv. Cryo. Eng. 42, 1 109 (1995).
34. J. D. McCambridge, N. D. Rizzo, X. S. Ling, J.-Q. Wang, D. E. Prober, L. R. Motowidlo, and B. A. Zeitlin, "Flux Pinning in NbTi/Nb Multilayers", IEEE Trans. Appl. Supercond. 5, 1697 (1995).
35. J.-Q. Wang and G. Xiao, "Finite Size Effect in Giant Magnetoresistance and Extraordinary Hall Effect in Magnetic Granular Solids", Phys. Rev. B 51, 5863 (1995).
36. J.-Q. Wang and G. Xiao, "The Origin of the Temperature Dependence of Giant Magnetoresistance in Magnetic Granular Solids", Phys. Rev. B 50, 3423 (1994).
37. J.-Q. Wang and G. Xiao, "Transition-Metal Granular Solid: Microstructure, Magnetic Properties, and Giant Magnetoresistance", Phys. Rev. B 49, 3982 (1994).
38. Y. Zhou, W. Lai, and J.-Q. Wang, "Calculated Electronic Structure of Metastable Phases of Cu", Phys. Rev. B 49, 4463 (1994).
39. J.-Q. Wang, E. Price, and G. Xiao, "Giant Magnetoresistance and its Dependence on Fabrication Conditions in Magnetic Alloys", J. Appl. Phys. 75, 6903 (1994).

40. G. Xiao and J.-Q. Wang, "Magnetic Properties of Metallic Fe and Co-Based Granular Alloys", J. Appl. Phys. 75, 6604 (1994).
41. M. N. Baibich, J. M. Broto, A. Fert, F. Nguyen van Dau, F. Petroff, P. Etienne, G. Creuzet, A. Friederich and J. Chazeles, "Giant Magnetoresistance of (OOl)Fe/(OOl)Cr Magnetic Superlattices", Phys. Rev. Lett., 61, (1988) 2472.
42. T. L. Altshler, "Application of Magnetic Force Microscopy in Magnetic Recording", in Atomic Force Microscopy/Scanning Tunneling Microscopy 2, edited S. H. Cohen and M. L. Lightbody, (Plenum, New York, 1997), p. 203.
43. S. S. P. Parlun, Z. G. Li and D. J. Smith, Appl. Phys. Lett., 3,(1991) 2710.
44. Florian Mansfeld, Monitoring of Atmospheric Corrosion Phenomena with Electrochemical Sensors, Material Science Department, University of Southern California, 1972.
45. S. K. Chawla, T. Anguish and J. H. Payer, Corrosion, 45 (1989): pp. 595-601.
46. F. H. Haynie and D. C. Stiles, Mater. Perform. August 1991, pp. 58-61.
47. P. J. Sereda, S. G. Croll and H. F. Slade, in "Atmospheric corrosion of Materials," ASTM STP-767, pp. 267-285, Eds. S. W. Dean, Jr. and E. C. Rhea, ASTM, Philadelphia, Pa., 1982.
48. F. Mansfeld, Proc. 8th Internat. Con. Congr. vol. 1, pp. 43-49, December, Germany, 1979.
49. F. Mansfeld and J. V. Kenkel, Corrosion, 33 (1977): p. 11; Corros. Sci., 18 (1976); p. 111.
50. W. H. Hartt, S. W. Smith, R. Lee, T. Chen and G. Sadasivan, NASA Proj. Rep. Florida Atlantic Univ., Boca Raton, 1987.
51. F. Ansuini, Project Report to Air Force Wright Aero. Labs., AFWALTR-88-4245, February 1989; Proc. Tri-Serv. Corrosion Conference, p. 48 1, NACE, Houston, Tex., 1987.
52. K. Fink and J. H. Payer, Paper #330, Corrosion-94, in "Pr0c.T-3L-18 Task Group Symp.", p. 1 16, NACE, Houston, Tex., 1994.
53. M. Murata and M. Karnakita, JP 03-122, 592 (5/91); JP 03-202798 (9/91); JP 03-223648 (10/91).
54. H. Ardakani, et al., J. Mat. Sci. Lett. 1933, 12(2), 63-65.
55. A. Hulanicki and A. Michalska, Electroanalysis, 1995, vol. 7, No. 7, p. 692-693.
56. K. Homa, et al., ASTM STP 1137, 1992, pp. 155-169.
57. P. K. Bhattacharya, Proc. of Internat. Conf. on Synchr. Rad. Sources, Indore, India, 3-6 February, 1992.
58. C. Khan Malek, Y. Vladimirsky, O. Vladimirsky, J. Scott, B. Craft and V. Saile, Rev. Sci. Instr. 67(9) Wrkshp I, 1-6, 1996.
59. S. S. Saxena, J. Tang, Y. S. Lee and C. J. O'Connor, "Magnetic and Magnetotransport Properties of Granular $Cu_{85}Fe_{15}$ Prepared by Mechanical Alloying," J. Appl. Phys., 76, (1994) 6820.
60. J. Tang, W. Zhao, C. Tao, C. J. O'Connor, L. Wang and M. Zhao, "Extended Solubility and Spin Glass Behavior in an Ag—Gd Solid Solution Prepared by Mechanical Alloying," Phys. Rev. B, 52, (1995) 12829.
61. W. Zhao, J. Tang, Y. S. Lee and C. J. O'Connor, "Synthesis and Superconductivity of Intermetallic Compounds $Y_2Ni_xB_{8-x}C_2$, $YNi_xCu_{2-x}B_2C$ and $YNi_xCu_{2-x}Si_2C$," J. Appl. Phys., 79, (1996) 5870.
62. P. Karri, A. Puri and J. Tang, "Large Room Temperature Magneto-Optical Kerr Effect in Magnetic Materials," IEEE Transactions on Magnetics, 32, (1996) 4099.
63. S. K. Dhar, Y. Kimura, M. Kozaki, R. Settai, Y. Onuki, W. Zhao and J. Tang, "The Magnetic Properties of $RNi_4Sn_2$ (R=La, Ce, Pr, Nd and Sm) Compounds," J. Phys. Soc. Japan., 66, (1997) 235.
64. J. Tang, "Magnetic Properties of a Few Materials Systems Made by Mechanical Alloying and Milling," Materials Science Forum, 235-238, (1997) 819.
65. M. Zhao, C. Sun, L. Wang, W. Li, Q. Su, W. Zhao and J. Tang, "Magnetic and Magnetotransport properties of Intermetallic 5 $mMn_2Si_2$," J. Appl. Phys., S 1, (1997) 5534.
66. J. Tang, W. Zhao, C. J. O'Connor and S. Li, "Nanocomposite Formation and Size Reduction of Terfenol-D Particles During Mechanical Milling," J. Alloys and Comp., 250, (1997) 482.
67. J. Tang, L. Feng, C. J. O'Connor and S. Li, "Antiferromagnetic Coupling in a Macroscopic Ferrimagnet EuS—Co", IEEE Transactions on Magnetics, 33, (1997) 3739.
68. J. Tang, J. S. Zabinski and J. E. Bultman, "TiC Coatings Prepared by Pulsed Laser Deposition and Magnetron Sputtering", Surface and Coatings Technology, 91, (1997) 69.

What is claimed is:

1. A corrosion and chemical thin film sensor, comprising:
a chemically exposed metal sensing portion sensitive to chemical exposure, in proximity to a component of a metallic structure or an electronic device sensitive to a corresponding chemical exposure;
a spin-valve comprising a giant magnetoresistive effect structure having a first magnetic layer and a second magnetic layer, the first and second magnetic layers being separated by a thin non-magnetic layer, wherein said chemically exposed metal sensing portion is at least one of the first and second magnetic layers;
a metallic magnetic or nonmagnetic buffer layer configured to induce nanotextured growth of the spin-valve, wherein the spin-valve is positioned on the buffer layer;
an integrated circuit attached to part of the spin-valve for determining a response of the exposed metal sensing portion to the chemical exposure; and
an output presenting a signal corresponding to the chemical exposure.

2. An electrical sensor, comprising:
a spin-valve comprising a giant magnetoresistive effect structure having a first magnetic layer and a second magnetic layer, the first and second magnetic layers being separated by a thin non-magnetic layer, wherein the spin-valve is positioned on a metallic buffer layer configured to induce nanotextured growth of the spin-valve; and
an integrated electrical circuit forming part of or attached to at least one magnetic layer or the buffer layer of the spin valve for sensing a magnetoresistance of the spin-valve;
at least one portion of an outer surface of the first and second magnetic layers is configured to undergo a change in magnetoresistance when said portion of the surface is chemically exposed to at least one chemical property of an environment or chemically interacts with the environment.

3. The sensor according to claim 2, wherein the at least one portion of the first and second magnetic layers which has the outer surface chemically exposed to the environment, corrodes in response to chemical exposure.

4. The sensor according to claim 2, wherein the at least one portion of the first and second magnetic layers which is chemically exposed to the environment produces a cumulative response to chemical exposure.

5. The sensor according to claim 2, wherein the at least one portion of the first and second magnetic layers which is chemically exposed to the environment is provided within a package having leads.

6. The sensor according to claim 2, wherein the at least one portion of the first and second magnetic layers which has the outer surface chemically exposed to the environment and has an electronic response which models an environmental response of a structural or functional component subject to environmental degradation.

7. The sensor according to claim 2, further comprising an output for producing signal corresponding to the chemical exposure of said outer surface of said layers to the environment, selectively responsive to the magnetoresistance of the spin valve.

8. The sensor according to claim 2, wherein the at least one chemical property comprises a corrosive tendency.

9. The sensor according to claim 2, wherein at least one of the first and second magnetic layers comprises a metal, and wherein the environment oxidizes the metal to alter a lower switching field and a higher switching field of the spin valve, to thereby alter an interaction of the first magnetic layer with the second magnetic layer.

10. The sensor according to claim 2, wherein the at least one chemical property comprises an analyte in the environment, wherein the sensor produces a time-weighted output in response to exposure to the analyte.

11. The sensor according to claim 10, wherein the analyte interacts with an enzyme, the enzyme generating a chemical species which interacts with at least one of the first and second magnetic layers.

12. The sensor according to claim 2, wherein the at least one of the first and second magnetic layers is irreversibly altered by the environment.

13. The sensor according to claim 2, wherein the at least one of the first and second magnetic layers is reversibly altered by the environment.

14. A method for sensing corrosion and chemical conditions, comprising:
(a) providing a spin-valve comprising a giant magnetoresistive effect structure having a first magnetic layer and a second magnetic layer, the first and second magnetic layers being separated by a thin non-magnetic layer;
(b) chemically exposing at least one of the first and second magnetic layers to an environment, to alter at least one property selected from the group consisting of:
(i) a lower switching field and a higher switching field of the spin-valve;
(ii) a magnetoresistance of the spin-valve, and
(iii) a giant magnetoresistive value of the spin-value;
(c) sensing the at least one altered property; and
(d) attaching an integrated electric circuit to the spin-valve forming an environmental control system for controlling an environmental exposure of the at least one chemically exposed first and second magnetic layers.

15. The method according to claim 14, wherein the environment comprises an analyte, wherein the at least one sensed altered property corresponds to a time-weighted output in response to exposure to the analyte.

16. The method according to claim 15, wherein the analyte interacts with an enzyme to generate a chemical species in relation to the analyte, the chemical species interacting with at least one of the first and second layers to alter the at least one property.

17. The method according to claim 14, wherein the at least one of the first and second magnetic layers is irreversibly altered by the environment.

18. The method according to claim 14, wherein the at least one of the first and second magnetic layers is reversibly altered by the environment.

19. The method according to claim 14, wherein the at least one of the first and second magnetic layers is nanotextured.

20. The method according to claim 14, wherein the environmental control system normalizes the exposure of the at least one of the first and second magnetic layers which is chemically exposed to the environment.

21. The method according to claim 14, wherein the giant magnetoresistive effect structure responds to chemical conditions in the environment which alter the at least one property of the at least one of the first and second magnetic layers which is chemically exposed to the environment.

* * * * *